United States Patent
Hiroi et al.

(10) Patent No.: US 10,669,445 B2
(45) Date of Patent: Jun. 2, 2020

(54) ION COMPLEX MATERIAL HAVING FUNCTION OF INHIBITING ADHESION OF BIOLOGICAL SUBSTANCE AND METHOD FOR MANUFACTURING THE SAME

(71) Applicant: NISSAN CHEMICAL INDUSTRIES, LTD., Tokyo (JP)

(72) Inventors: Yoshiomi Hiroi, Toyama (JP); Natsuki Abe, Shiraoka (JP); Taito Nishino, Shiraoka (JP); Masaki Kitahara, Shiraoka (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/535,049

(22) PCT Filed: Dec. 10, 2015

(86) PCT No.: PCT/JP2015/084597
§ 371 (c)(1),
(2) Date: Jun. 10, 2017

(87) PCT Pub. No.: WO2016/093293
PCT Pub. Date: Jun. 16, 2016

(65) Prior Publication Data
US 2017/0349777 A1     Dec. 7, 2017

(30) Foreign Application Priority Data
Dec. 10, 2014 (JP) ................. 2014-250269

(51) Int. Cl.
| | | |
|---|---|---|
| *C09D 143/02* | (2006.01) | |
| *C09D 133/14* | (2006.01) | |
| *C08F 230/02* | (2006.01) | |
| *C09D 5/00* | (2006.01) | |
| *C09D 5/16* | (2006.01) | |
| *A61L 27/34* | (2006.01) | |
| *A61L 31/10* | (2006.01) | |

(52) U.S. Cl.
CPC ............ *C09D 143/02* (2013.01); *A61L 27/34* (2013.01); *A61L 31/10* (2013.01); *C08F 230/02* (2013.01); *C09D 5/00* (2013.01); *C09D 5/1668* (2013.01)

(58) Field of Classification Search
CPC .......................... C09D 143/02; C09D 133/14
See application file for complete search history.

(56) References Cited

U.S. PATENT DOCUMENTS

| | | |
|---|---|---|
| 5,178,963 A | 1/1993 | Faust et al. |
| 2002/0000403 A1 | 1/2002 | Tanaka et al. |
| 2005/0148748 A1 | 7/2005 | Tanaka et al. |

(Continued)

FOREIGN PATENT DOCUMENTS

| | | |
|---|---|---|
| EP | 0173278 A2 | 3/1986 |
| JP | S57-010653 A | 1/1982 |

(Continued)

OTHER PUBLICATIONS

Machine-generated English translation of JP2014120410A.*

(Continued)

*Primary Examiner* — Vu A Nguyen
(74) *Attorney, Agent, or Firm* — Leydig, Voit & Mayer, Ltd.

(57) ABSTRACT

The present invention provides a copolymer obtainable by polymerizing a monomer mixture which contains at least compounds of the following formulae (A), (B) and (C), wherein $T^a$, $T^b$, $T^c$, $U^{a1}$, $U^{a2}$, $U^{b1}$, $U^{b2}$ and $U^{b3}$, $Q^a$, $Q^b$ and $Q^c$, $R^a$, $R^b$ and $R^c$, $An^-$ and m are as defined in Specification and Claims, and so on. The copolymer of the present invention can be utilized as an ion complex material excellent in a function of inhibiting adhesion of a biological substance.

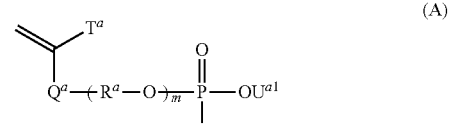

(A)

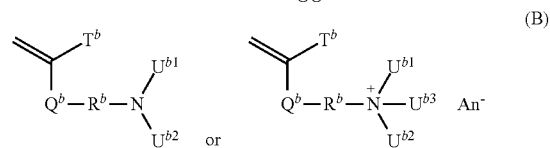

(B)

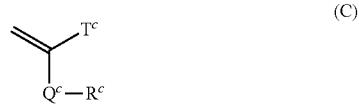

(C)

17 Claims, No Drawings

(56) References Cited

U.S. PATENT DOCUMENTS

| | | |
|---|---|---|
| 2010/0028286 A1 | 2/2010 | Carballada et al. |
| 2010/0292427 A1 | 11/2010 | Ban et al. |
| 2013/0150809 A1 | 6/2013 | Whiteford et al. |
| 2016/0115435 A1 | 4/2016 | Otani et al. |
| 2016/0122576 A1 | 5/2016 | Hiroi et al. |
| 2016/0129176 A1 | 5/2016 | Kanaki et al. |

FOREIGN PATENT DOCUMENTS

| | | |
|---|---|---|
| JP | H01-266126 A | 10/1989 |
| JP | H06-092979 A | 4/1994 |
| JP | H07-215814 A | 8/1995 |
| JP | 2001-279164 A | 10/2001 |
| JP | 2001-323030 A | 11/2001 |
| JP | 2007-063459 A | 3/2007 |
| JP | 2009-057549 A | 3/2009 |
| JP | 2010-233999 A | 10/2010 |
| JP | 2014-120410 A | 6/2014 |
| WO | WO 2012/172291 A1 | 12/2012 |
| WO | WO 2014/196650 A1 | 12/2014 |
| WO | WO 2014/196651 A1 | 12/2014 |

OTHER PUBLICATIONS

Computer-generated English-language translation of JP 2001/279164 A to Nakajima et al.*
Sakiyama et al., *Japanese Journal of Artificial Organs*, 39(1): 77-80 (2010).
Xu et al., *Japanese Journal of Polymer Science and Technology*, 65(3): 228-234 (Mar. 2008).
Japanese Patent Office, International Search Report in International Patent Application No. PCT/JP2015/084597 (dated Feb. 9, 2016).
European Patent Office, Extended European Search Report in European Patent Application No. 15866457.3 (dated May 3, 2018).
Chinese Patent Office, The First Office Action in Chinese Patent Application No. 201580066417.0 (dated Mar. 4, 2019).

* cited by examiner

ION COMPLEX MATERIAL HAVING FUNCTION OF INHIBITING ADHESION OF BIOLOGICAL SUBSTANCE AND METHOD FOR MANUFACTURING THE SAME

CROSS-REFERENCE TO RELATED APPLICATIONS

This patent application is the U.S. national phase of International Patent Application No. PCT/JP2015/084597, filed on Dec. 10, 2015, which claims the benefit of Japanese Patent Application No. 2014-250269, filed Dec. 10, 2014, the disclosures of which are incorporated herein by reference in their entireties for all purposes.

TECHNICAL FIELD

The present invention relates to an ion complex material having a function of inhibiting adhesion of a biological substance and a method for manufacturing the same. More specifically, the present invention relates to a coating film having a function of inhibiting adhesion of a biological substance, a method for manufacturing the coating film, a copolymer obtainable by polymerizing a specific monomer mixture, a method for producing the copolymer, a composition for forming a coating film having a specific composition, a method for producing a varnish containing a copolymer to be used as a raw material of the composition for forming a coating film which is used for forming said film, a sol for forming the coating film, and a method for manufacturing the sol.

BACKGROUND ART

For suppressing adhesion of a biological substance to medical instruments, equipment, etc., such as an artificial dialyzer, artificial organs, medical equipment, etc., various coating materials having a function of inhibiting adhesion of a biological substance have been proposed. Among these, it has been known a material of inhibiting adhesion of a biological substance by coating a polymer having an ethylene glycol chain at the side chain and, for example, in Patent Document 1, examples of coating a copolymer of 2-methoxyethyl acrylate onto nonwoven fabric such as a blood filter and a dialysis filter, etc., have been disclosed. Also, in Non-Patent Document 1, to impart a function of inhibiting adhesion of a biological substance to polysulfone (PSF) or polyether sulfone (PES), etc., which is used as a substrate for an artificial dialysis film, it has been disclosed that polyvinylpyrrolidone (PVP) having a hydrophilic property is coated thereon. However, while these materials have a function of inhibiting adhesion of a biological substance which is expected due to the effect of the hydrophilic property, etc., solubility of the polymer itself to water is suppressed and solubility in an alcohol or an organic solvent is heightened, elution of the coating film itself has been identified by the causes of washing with ethanol, etc., for sterilization, shear stress (shearing stress) to the coating film by a high viscosity biological substance, etc., and use for a long period of time, etc., and yet allergy, etc., due to the eluate is a matter of concern.

On the other hand, a material having a polymer material containing a cation and an anion at the side chain on the surface thereof has been known to have a function of preventing adsorption of a biological substance (protein, cell, etc.) by being maintained to electrically neutral at the surface thereof due to electrostatic balance. In addition, it has also been proposed a coating material using such a function, and various reports have been made on the fixation or immobilization method to glass or a polymer substrate, etc. For example, in Non-Patent Document 2, it has been reported that surface modification was accomplished by chemical adsorption with a glass substrate using a polymer obtained by copolymerizing 2-methacryloyloxyethyl phosphoryl choline (MPC) having a similar molecular structure to a phospholipid as a charge neutralization unit and 3-(trimethoxysilyl)propyl methacrylate having a silane coupling group. On the other hand, it has also been reported that onto a polymer substrate, a polymer into which butyl methacrylate has been copolymerized is to be fixed onto the substrate by aiming physical adsorption due to hydrophobic interaction. However, according to these methods, it is necessary to select a kind of the polymer depending on a kind of the substrate.

Also, in Patent Document 2, a coating film which is obtained from a film formed from a coating solution containing a polymer having a phosphate group by subjecting to heat treatment at 200 to 450° C. has been disclosed. To suppress elution of the coating film into an aqueous medium, it is necessary to carry out heat treatment at a high temperature of 200 to 450° C. after coating onto a substrate, so that a heating device such as an oven, a hot plate, etc., is necessary for the heat treatment. In addition, there was a problem that it could be difficultly applied to a substrate having low heat resistance such as a resin material, etc. Further, various polymers have been polymerized to manufacture a coating solution for forming a coating film, but in the Examples, polymerization reaction was carried out in ethanol, and polymerization reactivity in water was unclear.

Further, in Patent Document 3, there are disclosed a novel acrylic phosphate amine salt monomer (half salt) obtained by reacting an amine with an acrylic acidic phosphate monomer in the presence of water to selectively proceed an acid-base reaction and a method for manufacturing the same. The amine salt (half salt) has been disclosed to have a wide range of uses and usefulness in the field of a photosensitive resin as a monomer for providing rubber elasticity or a modifier of an oil-soluble substance, but it is unclear about polymerization reactivity of the amine salt (half salt) monomer itself in water, and a function of inhibiting adhesion of the obtained polymer to a biological substance. In addition, a used ratio of the above-mentioned acrylic acidic phosphate monomer in the whole used monomer at the time of polymerization in a polar solvent such as methanol, etc., is mainly around 5% to around 1% in many examples, and there is disclosed that if an amount is larger, the product is gelled.

Moreover, in Patent Document 4, a blood purifier having a hollow fiber film containing polyvinylpyrrolidone (PVP) has been disclosed, a mode diameter at the peak which is residing at the largest diameter in the particle diameter distribution measured by the dynamic light scattering method of the PVP in the hollow fiber has been disclosed to be 300 nm or less, and to coat the inside of the hollow fiber using the PVP coating liquid has been disclosed.

PRIOR ART DOCUMENTS

Patent Documents

Patent Document 1: JP 2001-323030A
Patent Document 2: JP 2007-63459A
Patent Document 3: JP Hei. 6-92979A
Patent Document 4: JP 2010-233999A Non-Patent Documents Non-Patent Document 1: The Japanese Journal of Artificial Organs, Vol. 39, No. 1, p. 77 (2010)
Non-Patent Document 2: Japanese Journal of Polymer Science and Technology, Vol. 65, No. 3, p. 228 (2008)

SUMMARY OF THE INVENTION

Problems to be Solved by the Invention

The present inventors studied until now to overcome the above-mentioned three problems that (1) a coating film obtainable by a heat treatment at high temperature of 200 to 450° C. is required to suppress elution thereof into an aqueous medium, (2) a material of the coating film is required to be suitably selected depending on the kind of the substrate, and (3) a copolymer to be used in the above-mentioned composition for forming a coating film is easily gelled at the time of manufacturing a varnish. An object of the present invention is, in addition to solve the above-mentioned problems, to further improve a function of inhibiting adhesion of a biological substance in a coating film, and to improve a handling property of the composition for forming a coating film in the manufacture thereof, in particular, to provide a coating film having a function of inhibiting adhesion of a biological substance which can be easily formed only by a low temperature drying process, a method for manufacturing the coating film, a copolymer obtainable by polymerizing a specific monomer mixture, a method for producing the copolymer, a composition for forming a coating film having a specific composition, a method for producing a varnish containing the copolymer to be used as a raw material of a composition for forming a coating film for forming the film, a sol for forming the coating film, and a method for producing the sol.

Means to Solve the Problems

The present inventions are as follows:
1. A copolymer which is obtainable by polymerizing a monomer mixture which contains at least compounds of the following formulae (A), (B) and (C):

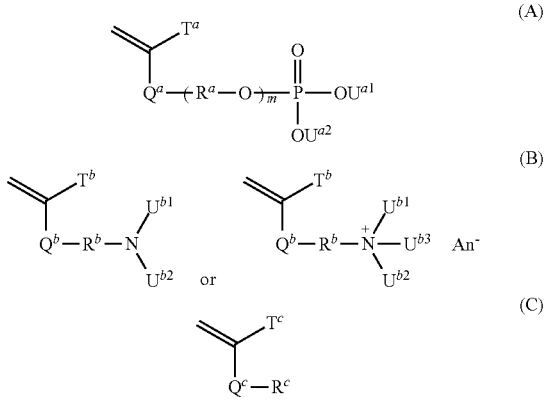

[wherein
$T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;

$Q^a$ and $Q^b$ each independently represent a single bond, an ester bond or an amide bond, $Q^c$ represents a single bond, an ether bond or an ester bond;
$R^a$ and $R^b$ each independently represent a linear or branched alkylene group having 1 to 10 carbon atoms which may be substituted by a halogen atom(s), $R^c$ represents a linear or branched alkyl group having 1 to 18 carbon atoms, a cyclic hydrocarbon group having 3 to 10 carbon atoms, an aryl group having 6 to 10 carbon atoms, an aralkyl group having 7 to 14 carbon atoms or an aryloxyalkyl group having 7 to 14 carbon atoms (here, the above-mentioned aryl portion may be substituted by a linear or branched alkyl group having 1 to 5 carbon atoms which may be substituted by a halogen atom(s));
$An^-$ represents an anion selected from the group consisting of a halide ion, an inorganic acid ion, a hydroxide ion and an isothiocyanate ion; and
m represents an integer of 0 to 6];
2. the copolymer described in the above-mentioned 1, wherein the copolymer is obtainable by polymerizing a monomer mixture further containing a compound of the following formula (D) or (E):

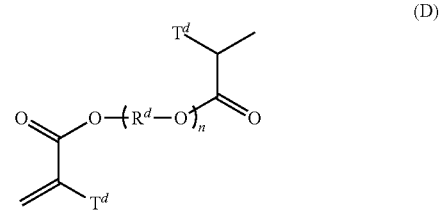

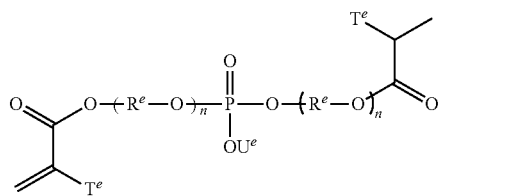

[wherein
$T^d$, $T^e$ and $U^e$ each independently represent a hydrogen atom or a linear or branched alkyl group having 1 to 5 carbon atoms;
$R^d$ and $R^e$ each independently represent a linear or branched alkylene group having 1 to 10 carbon atoms which may be substituted by a halogen atom(s); and n represents an integer of 1 to 6];
3. a composition for forming a coating film which contains
(i) a copolymer which contains a recurring unit containing an organic group of the following formula (a), a recurring unit containing an organic group of the following formula (b) and a recurring unit containing an organic group of the following formula (c):

-continued

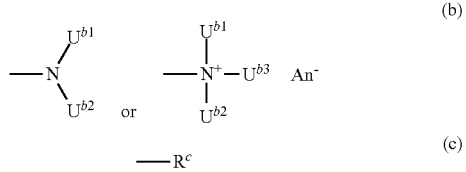

[wherein
$U^{a1}$, $U^{a2}$, $U^{b1}$, $U^{b2}$ and $U^{b3}$ each independently represent a hydrogen atom or a linear or branched alkyl group having 1 to 5 carbon atoms;
$R^c$ represents a linear or branched alkyl group having 4 to 18 carbon atoms, a cyclic hydrocarbon group having 3 to 10 carbon atoms, an aryl group having 6 to 10 carbon atoms, an aralkyl group having 7 to 14 carbon atoms or an aryloxyalkyl group having 7 to 14 carbon atoms (here, the above-mentioned aryl portion may be substituted by a linear or branched alkyl group having 1 to 5 carbon atoms which may be substituted by a halogen atom(s));
An⁻ represents an anion selected from the group consisting of a halide ion, an inorganic acid ion, a hydroxide ion and an isothiocyanate ion; and
(ii) a solvent;

4. the composition described in the above-mentioned 3, wherein the copolymer contains recurring units of the following formulae (a1), (b1) and (c1):

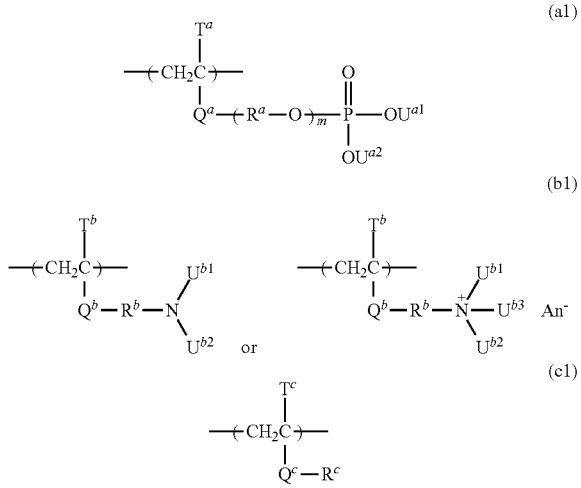

[wherein
$T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;
$Q^a$ and $Q^b$ each independently represent a single bond, an ester bond or an amide bond, $Q^c$ represents a single bond, an ether bond or an ester bond;
$R^a$ and $R^b$ each independently represent a linear or branched alkylene group having 1 to 10 carbon atoms which may be substituted by a halogen atom(s), $R^c$ represents a linear or branched alkyl group having 4 to 18 carbon atoms, an alicyclic hydrocarbon group having 3 to 10 carbon atoms, an aryl group having 6 to 10 carbon atoms, an aralkyl group having 7 to 14 carbon atoms or an aryloxyalkyl group having 7 to 14 carbon atoms (here, the above-mentioned aryl portion may be substituted by a linear or branched alkyl group having 1 to 5 carbon atoms which may be substituted by a halogen atom(s));

An⁻ represents an anion selected from the group consisting of a halide ion, an inorganic acid ion, a hydroxide ion and an isothiocyanate ion; and
m represents an integer of 0 to 6];

5. a coating film obtainable by a method which comprises a process of coating a composition for forming a coating film containing a copolymer which contains a recurring unit containing an organic group of the following formula (a), a recurring unit containing an organic group of the following formula (b) and a recurring unit containing an organic group of the following formula (c):

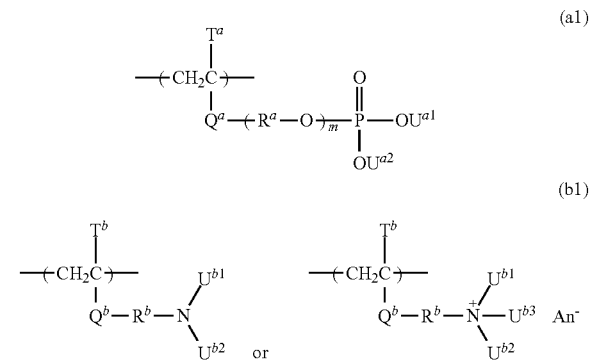

[wherein
$U^{a1}$, $U^{a2}$, $U^{b1}$, $U^{b2}$ and $U^{b3}$ each independently represent a hydrogen atom or a linear or branched alkyl group having 1 to 5 carbon atoms;
$R^c$ represents a linear or branched alkyl group having 4 to 18 carbon atoms, an alicyclic hydrocarbon group having 3 to 10 carbon atoms, an aryl group having 6 to 10 carbon atoms, an aralkyl group having 7 to 14 carbon atoms or an aryloxyalkyl group having 7 to 14 carbon atoms (here, the above-mentioned aryl portion may be substituted by a linear or branched alkyl group having 1 to 5 carbon atoms which may be substituted by a halogen atom(s));
An⁻ represents an anion selected from the group consisting of a halide ion, an inorganic acid ion, a hydroxide ion and an isothiocyanate ion], and
a solvent,
onto a substrate;

6. the coating film described in the above-mentioned 5, wherein the copolymer contains recurring units of the following formulae (a1), (b1) and (c1):

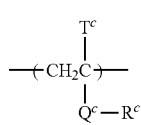

[wherein
$T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;
$Q^a$ and $Q^b$ each independently represent a single bond, an ester bond or an amide bond, $Q^c$ represents a single bond, an ether bond or an ester bond;
$R^a$ and $R^b$ each independently represent a linear or branched alkylene group having 1 to 10 carbon atoms which may be substituted by a halogen atom(s), $R^c$ represents a linear or branched alkyl group having 4 to 18 carbon atoms, an alicyclic hydrocarbon group having 3 to 10 carbon atoms, an aryl group having 6 to 10 carbon atoms, an aralkyl group having 7 to 14 carbon atoms or an aryloxyalkyl group having 7 to 14 carbon atoms (here, the above-mentioned aryl portion may be substituted by a linear or branched alkyl group having 1 to 5 carbon atoms which may be substituted by a halogen atom(s));
An⁻ represents an anion selected from the group consisting of a halide ion, an inorganic acid ion, a hydroxide ion and an isothiocyanate ion; and
m represents an integer of 0 to 6;

7. the coating film described in the above-mentioned 5 or 6, wherein the method further comprises a process of previously adjusting a pH of the composition for forming the coating film;

8. the coating film described in any one of the above-mentioned 5 to 7, wherein the method further comprises a process of washing a film obtained after a drying process with at least one solvent selected from the group consisting of water and an aqueous solution containing an electrolyte(s);

9. the coating film described in any one of the above-mentioned 5 to 8, wherein the film has a function of inhibiting adhesion of a biological substance(s);

10. a sol comprising a copolymer which contains a recurring unit containing an organic group of the following formula (a), a recurring unit containing an organic group of the following formula (b) and a recurring unit containing an organic group of the following formula (c):

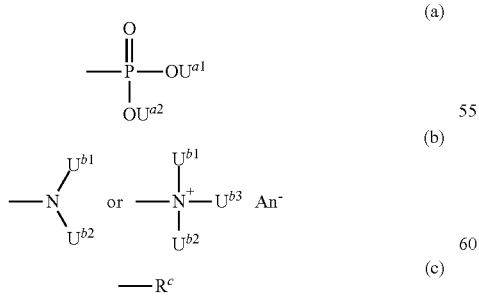

[wherein
$U^{a1}$, $U^{a2}$, $U^{b1}$, $U^{b2}$ and $U^{b3}$ each independently represent a hydrogen atom or a linear or branched alkyl group having 1 to 5 carbon atoms;
$R^c$ represents a linear or branched alkyl group having 4 to 18 carbon atoms, an alicyclic hydrocarbon group having 3 to 10 carbon atoms, an aryl group having 6 to 10 carbon atoms, an aralkyl group having 7 to 14 carbon atoms or an aryloxyalkyl group having 7 to 14 carbon atoms (here, the above-mentioned aryl portion may be substituted by a linear or branched alkyl group having 1 to 5 carbon atoms which may be substituted by a halogen atom(s));
An⁻ represents an anion selected from the group consisting of a halide ion, an inorganic acid ion, a hydroxide ion and an isothiocyanate ion];

11. the sol described in the above-mentioned 10, wherein an average particle diameter in particle diameter distribution measured by a dynamic light scattering method is 2 nm or more and 500 nm or less;

12. a method for manufacturing a coating film which comprises a process of coating a composition for forming the coating film containing a copolymer which contains a recurring unit containing an organic group of the following formula (a), a recurring unit containing an organic group of the following formula (b) and a recurring unit containing an organic group of the following formula (c):

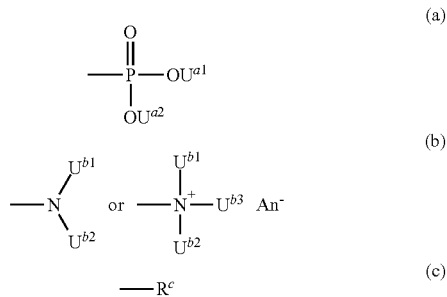

[wherein
$U^{a1}$, $U^{a2}$, $U^{b1}$, $U^{b2}$ and $U^{b3}$ each independently represent a hydrogen atom or a linear or branched alkyl group having 1 to 5 carbon atoms;
$R^c$ represents a linear or branched alkyl group having 4 to 18 carbon atoms, a cycloalkyl group having 3 to 8 carbon atoms, an aryl group having 6 to 10 carbon atoms, an aralkyl group having 7 to 14 carbon atoms or an aryloxyalkyl group having 7 to 14 carbon atoms (here, the above-mentioned aryl portion may be substituted by a linear or branched alkyl group having 1 to 5 carbon atoms which may be substituted by a halogen atom(s));
An⁻ represents an anion selected from the group consisting of a halide ion, an inorganic acid ion, a hydroxide ion and an isothiocyanate ion], and
a solvent, onto a substrate;

13. a method for producing a varnish containing a copolymer which comprises a process of adding dropwise a mixture containing compounds of the following formulae (A), (B) and (C):

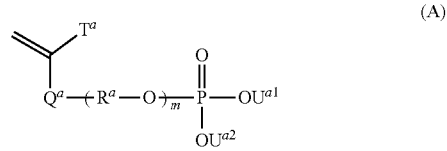

-continued

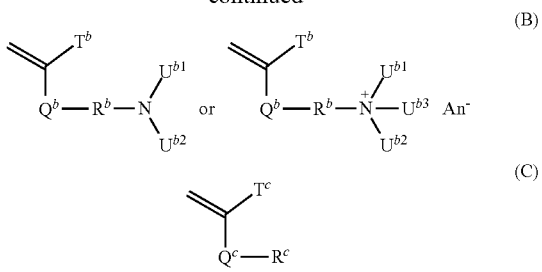

[wherein
$T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;
$Q^a$ and $Q^b$ each independently represent a single bond, an ester bond or an amide bond, $Q^c$ represents a single bond, an ether bond or an ester bond;
$R^a$ and $R^b$ each independently represent a linear or branched alkylene group having 1 to 10 carbon atoms which may be substituted by a halogen atom(s), $R^c$ represents a linear or branched alkyl group having 4 to 18 carbon atoms, an alicyclic hydrocarbon group having 3 to 10 carbon atoms, an aryl group having 6 to 10 carbon atoms, an aralkyl group having 7 to 14 carbon atoms or an aryloxyalkyl group having 7 to 14 carbon atoms (here, the above-mentioned aryl portion may be substituted by a linear or branched alkyl group having 1 to 5 carbon atoms which may be substituted by a halogen atom(s));
An⁻ represents an anion selected from the group consisting of a halide ion, an inorganic acid ion, a hydroxide ion and an isothiocyanate ion;
and m represents an integer of 0 to 6],
a solvent and a polymerization initiator
to a solvent which has been maintained at a temperature higher than a 10 hour half-life temperature of the polymerization initiator, and reacting these;

14. a method for producing a copolymer which comprises a process of polymerizing a monomer mixture containing at least compounds of the following formulae (A), (B) and (C):

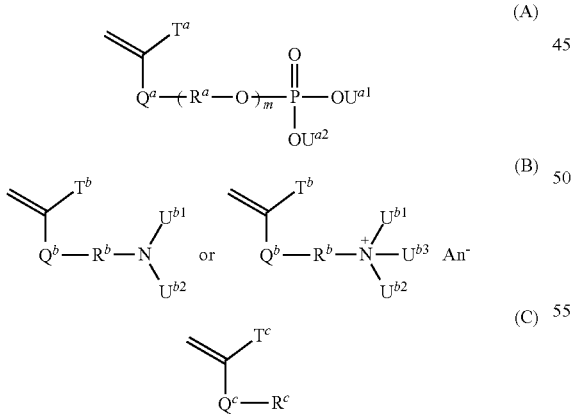

[wherein
$T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;
$Q^a$ and $Q^b$ each independently represent a single bond, an ester bond or an amide bond, $Q^c$ represents a single bond, an ether bond or an ester bond;
$R^a$ and $R^b$ each independently represent a linear or branched alkylene group having 1 to 10 carbon atoms which may be substituted by a halogen atom(s), $R^c$ represents a linear or branched alkyl group having 1 to 18 carbon atoms, a cyclic hydrocarbon group having 3 to 10 carbon atoms, an aryl group having 6 to 10 carbon atoms, an aralkyl group having 7 to 14 carbon atoms or an aryloxyalkyl group having 7 to 14 carbon atoms (here, the above-mentioned aryl portion may be substituted by a linear or branched alkyl group having 1 to 5 carbon atoms which may be substituted by a halogen atom(s));
An⁻ represents an anion selected from the group consisting of a halide ion, an inorganic acid ion, a hydroxide ion and an isothiocyanate ion; and
m represents an integer of 0 to 6];

15. the producing method described in the above-mentioned 14, wherein the copolymer is obtained by polymerizing a monomer mixture further containing a compound of the following formula (D) or (E):

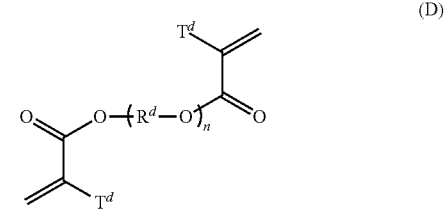

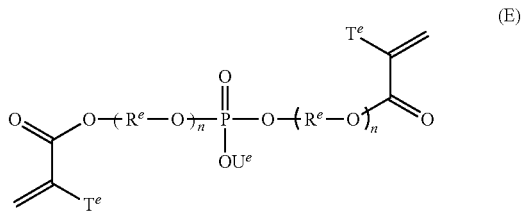

[wherein
$T^d$, $T^e$ and $U^e$ each independently represent a hydrogen atom or a linear or branched alkyl group having 1 to 5 carbon atoms;
$R^d$ and $R^e$ each independently represent a linear or branched alkylene group having 1 to 10 carbon atoms which may be substituted by a halogen atom(s); and n represents an integer of 1 to 6];

16. a method for producing a sol which comprises a process of polymerizing a monomer mixture containing at least compounds of the following formulae (A), (B) and (C):

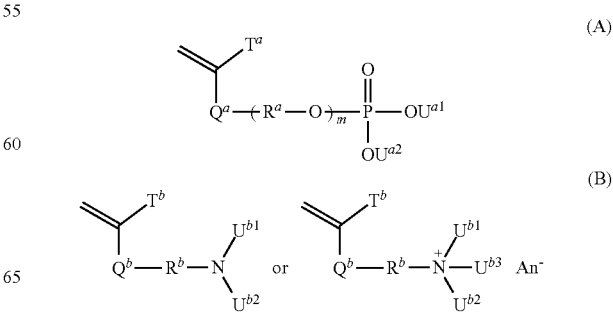

-continued

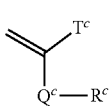

(C)

[wherein $T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;

$Q^a$ and $Q^b$ each independently represent a single bond, an ester bond or an amide bond, $Q^c$ represents a single bond, an ether bond or an ester bond;

$R^a$ and $R^b$ each independently represent a linear or branched alkylene group having 1 to 10 carbon atoms which may be substituted by a halogen atom(s), $R^c$ represents a linear or branched alkyl group having 1 to 18 carbon atoms, a cyclic hydrocarbon group having 3 to 10 carbon atoms, an aryl group having 6 to 10 carbon atoms, an aralkyl group having 7 to 14 carbon atoms or an aryloxyalkyl group having 7 to 14 carbon atoms (here, the above-mentioned aryl portion may be substituted by a linear or branched alkyl group having 1 to 5 carbon atoms which may be substituted by a halogen atom(s));

$An^-$ represents an anion selected from the group consisting of a halide ion, an inorganic acid ion, a hydroxide ion and an isothiocyanate ion; and m represents an integer of 0 to 6];

17. the copolymer described in the above-mentioned 1 or 2, which is for forming a coating film having a function of inhibiting adhesion of a biological substance;

18. the composition described in the above-mentioned 3 or 4, which is for forming a coating film having a function of inhibiting adhesion of a biological substance;

19. the sol described in the above-mentioned 10 or 11, which is for forming a coating film having a function of inhibiting adhesion of a biological substance;

20. the manufacturing method described in the above-mentioned 12, wherein the coating film has a function of inhibiting adhesion of a biological substance;

21. the producing method described in the above-mentioned 13, wherein the varnish is for forming a coating film having a function of inhibiting adhesion of a biological substance;

22. the producing method described in the above-mentioned 14 or 15, wherein the copolymer is for forming a coating film having a function of inhibiting adhesion of a biological substance;

23. the producing method described in the above-mentioned 16, wherein the sol is for forming a coating film having a function of inhibiting adhesion of a biological substance.

Effects of the Invention

The coating film of the present invention can be formed by subjecting to a process of coating a composition for forming a coating film containing a copolymer which contains an anion of the formula (a), a cation of the formula (b) and a hydrophobic group of the formula (c), and a solvent on a substrate. The coating film of the present invention can be firmly fixed without selecting a kind of the substrate such as glass, a metal containing compound, a semi-metal containing compound and a resin (a synthetic resin and a natural resin), etc., by forming an ionic bonding (ion complex) of the anion of the formula (a) and the cation of the formula (b), and after fixation, it gives a coating film excellent in durability against an aqueous solvent (water, a phosphate buffered physiological saline (PBS), an alcohol, etc.). Further, it becomes a film having good adhesiveness with a resin such as plastics, etc., and more excellent in durability to an aqueous solvent after fixing by incorporating the hydrophobic group of the formula (c). Also, it gives a coating film excellent in a function of inhibiting adhesion of a biological substance by previously adjusting a pH of the composition for forming a coating film with a pH adjusting agent, etc., or by washing the coating film after drying with water and/or an aqueous solution containing an electrolyte(s), for controlling ion balance of the copolymer.

In addition, the copolymer of the present invention is improved in solubility to an organic solvent by containing a hydrophobic group of the formula (c) in addition to a cation of the formula (a) and the cation of the formula (b). According to this constitution, the solvent of the composition for forming a coating film containing the copolymer can be selected from a wide range according to the desired properties of the composition and, for example, by using, as a solvent, an organic solvent such as ethanol, etc., which is easily volatilized as compared with water, the coating process is simplified such as drying after the coating becomes easy, etc. In addition, since the copolymer contains a hydrophobic group of the formula (c), improvement in a function of inhibiting adhesion of a biological substance of the coating film can be accomplished.

Further, when the copolymer contained in the composition for forming a coating film of the present invention is to be synthesized, a phosphate group which is a side chain of the copolymer has been known, for example, as disclosed in Patent document 3, to have strong association property so that it sometimes gelled depending on the polymerization conditions, but in the present invention, a method for manufacturing a transparent varnish containing a copolymer without gelation can be provided by controlling an order of addition of a reactant or a reagent or a temperature at the time of the addition. According to this method, even if it is a polymer containing a recurring unit having a phosphate group in the copolymer according to the present invention in an amount of, for example, 50 mol % or so, and a transparent varnish containing a copolymer can be manufactured without gelation. The varnish containing the copolymer can be used as a composition for forming a coating film which is used for forming the coating film of the present invention, or a raw material for preparing the same.

EMBODIMENTS TO CARRY OUT THE INVENTION

Explanation of the Terms

The terms used in the present invention have the following definitions, otherwise specifically mentioned.

In the present invention, the "halogen atom" means a fluorine atom, a chlorine atom, a bromine atom or an iodine atom.

In the present invention, the "alkyl group" means a monovalent group of linear or branched, saturated aliphatic hydrocarbon. The "linear or branched alkyl group having 1 to 5 carbon atoms" may be mentioned, for example, a methyl group, an ethyl group, an n-propyl group, an isopropyl group, an n-butyl group, an isobutyl group, an s-butyl group, a t-butyl group, an n-pentyl group, a 1-methylbutyl group, a 2-methylbutyl group, a 3-methylbutyl group, a 1,1-dimethylpropyl group, a 1,2-dimethylpropyl group, a 2,2-dimethylpropyl group or a 1-ethylpropyl group. The "linear or branched alkyl group having 1 to 18 carbon atoms" may be mentioned, in addition to the examples of the "linear or branched alkyl group having 1 to 5 carbon atoms", a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group or an octadecyl group, or an isomer thereof.

In the present invention, the "linear or branched alkyl group having 1 to 5 carbon atoms which may be substituted by a halogen atom(s)" means either the above-mentioned linear or branched alkyl group having 1 to 5 carbon atoms, or the above-mentioned linear or branched alkyl group having 1 to 5 carbon atoms substituted by one or more of the above-mentioned halogen atoms. Examples of the "linear or branched alkyl group having 1 to 5 carbon atoms" are as mentioned above. On the other hand, the "linear or branched alkyl group having 1 to 5 carbon atoms substituted by one or more halogen atoms" means a group in which one or more optional hydrogen atoms of the above-mentioned linear or branched alkyl group having 1 to 5 carbon atoms is/are replaced by a halogen atom(s), and examples thereof may be mentioned a fluoromethyl group, a difluoromethyl group, a trifluoromethyl group, a chloromethyl group, a dichloromethyl group, a trichloromethyl group, a bromomethyl group, an iodomethyl group, a 2,2,2-trifluoroethyl group, a 2,2,2-trichloroethyl group, a perfluoroethyl group, a perfluorobutyl group or a perfluoropentyl group, etc.

In the present invention, the "ester bond" means —C(=O)—O— or —O—C(=O)—, the "amide bond" means —NHC(=O)— or —C(=O)NH— and the ether bond means —O—.

In the present invention, the "linear or branched alkylene group having 1 to 10 carbon atoms which may be substituted by a halogen atom(s)" means a linear or branched alkylene group having 1 to 10 carbon atoms or a linear or branched alkylene group having 1 to 10 carbon atoms substituted by one or more halogen atoms. Here, the "alkylene group" means a divalent organic group corresponding to the above-mentioned alkyl group. Examples of the "linear or branched alkylene group having 1 to 10 carbon atoms" may be mentioned a methylene group, an ethylene group, a propylene group, a trimethylene group, a tetramethylene group, a 1-methylpropylene group, a 2-methylpropylene group, a dimethylethylene group, an ethylethylene group, a pentamethylene group, a 1-methyl-tetramethylene group, a 2-methyl-tetramethylene group, a 1,1-dimethyl-trimethylene group, a 1,2-dimethyl-trimethylene group, a 2,2-dimethyl-trimethylene group, a 1-ethyl-trimethylene group, a hexamethylene group, an octamethylene group and a decamethylene group, etc., among these, an ethylene group, a propylene group, an octamethylene group and a decamethylene group are preferred, and, for example, a linear or branched alkylene group having 1 to 5 carbon atoms such as an ethylene group, a propylene group, a trimethylene group, a tetramethylene group, etc., are more preferred, and, in particular, an ethylene group or a propylene group is preferred. The "linear or branched alkylene group having 1 to 10 carbon atoms substituted by one or more halogen atoms" means a group in which one or more optional hydrogen atoms of the above-mentioned alkylene group is/are replaced by a halogen atom(s), and, in particular, a part or whole of the hydrogen atom(s) of the ethylene group or the propylene group is/are replaced by a halogen atom(s) is/are preferred.

In the present invention, the "cyclic hydrocarbon group having 3 to 10 carbon atoms" means a monovalent group of monocyclic or polycyclic, saturated or partially unsaturated, aliphatic hydrocarbon having 3 to 10 carbon atoms. Among these, a monocyclic or bicyclic, saturated monovalent aliphatic hydrocarbon group having 3 to 10 carbon atoms is preferred, and there may be mentioned, for example, a cycloalkyl group having 3 to 10 carbon atoms such as a cyclopropyl group, a cyclobutyl group and a cyclohexyl group, etc., or a bicycloalkyl group having 4 to 10 carbon atoms such as a bicyclo[3.2.1]octyl group, a bornyl group and an isobornyl group, etc.

In the present invention, the "aryl group having 6 to 10 carbon atoms" means a monovalent group of monocyclic or polycyclic, aromatic hydrocarbon having 6 to 10 carbon atoms, and there may be mentioned, for example, a phenyl group, a naphthyl group or an anthryl group, etc. The "aryl group having 6 to 10 carbon atoms" may be substituted by one or more of the above-mentioned "linear or branched alkyl group having 1 to 5 carbon atoms which may be substituted by a halogen atom(s)."

In the present invention, the "aralkyl group having 7 to 14 carbon atoms" means a group —R—R' (in which R represents the above-mentioned "alkylene group having 1 to 5 carbon atoms", and R' represents the above-mentioned "aryl group having 6 to 10 carbon atoms"), and there may be mentioned, for example, a benzyl group, a phenethyl group, or an α-methylbenzyl group, etc. The aryl portion of the "aralkyl group having 7 to 14 carbon atoms" may be substituted by one or more of the above-mentioned "linear or branched alkyl group having 1 to 5 carbon atoms which may be substituted by a halogen atom(s)."

In the present invention, the "aryloxyalkyl group having 7 to 14 carbon atoms" means a group —R—O—R' (in which R represents the above-mentioned alkylene group having 1 to 5 carbon atoms", and R' represents the above-mentioned "aryl group having 6 to 10 carbon atoms"), and there may be mentioned, for example, a phenoxymethyl group, a phenoxyethyl group, or a phenoxypropyl group, etc. The aryl portion of the "aryloxyalkyl group having 7 to 14 carbon atoms" may be substituted by one or more of the above-mentioned "linear or branched alkyl group having 1 to 5 carbon atoms which may be substituted by a halogen atom(s)."

In the present invention, "a halide ion" means a fluoride ion, a chloride ion, a bromide ion or an iodide ion.

In the present invention, "an inorganic acid ion" means a carbonate ion, a sulfate ion, a phosphate ion, a hydrogen phosphate ion, a dihydrogen phosphate ion, a nitrate ion, a perchlorate ion or a borate ion.

As the above-mentioned $An^-$, preferred are a halide ion, a sulfate ion, a phosphate ion, a hydroxide ion and an isothiocyanate ion, and particularly preferred is a halide ion.

In the present invention, the (meth)acrylate compound means both of an acrylate compound and a methacrylate compound. For example, the (meth)acrylic acid means acrylic acid and methacrylic acid.

In the present invention, the biological substance may be mentioned a protein, a saccharide, a nucleic acid and a cell or a combination thereof. The protein may be mentioned, for example, fibrinogen, bovine serum albumin (BSA), human albumin, various kinds of globulins, β-lipoprotein, various kinds of antibodies (IgG, IgA, IgM), peroxidase, various kinds of complements, various kinds of lectins, fibronectin, lysozyme, von Willebrand factor (vWF), serum γ-globulin, pepsin, ovalbumin, insulin, histone, ribonuclease, collagen and cytochrome c, the saccharide may be mentioned, for example, glucose, galactose, mannose, fructose, heparin and hyaluronic acid, the nucleic acid may be mentioned, for example, deoxyribonucleic acid (DNA) and ribonucleic acid (RNA), the cell may be mentioned, for example, fibroblast, bone marrow cells, B lymphocytes, T lymphocytes, neutrophils, red blood cells, platelets, macrophages, monocytes, bone cells, pericytes, dendritic cells, keratinocytes, fat cells, mesenchymal cells, epithelial cells, epidermal cells, endothelial cells, vascular endothelial cells, hepatic parenchymal cells, cartilage cells, cumulus cells, neural cells, glial cells, neurons, oligodendrocyte, microglia, astroglial cells, heart cells, esophagus cells, muscle cells (for example, smooth muscle cells or skeletal muscle cells), pancreatic beta cells, melanocytes, hematopoietic precursor cells, mononuclear cells, embryonic stem cells (ES cell), embryonic tumor cells, embryonic germline stem cells, induced pluripotent stem cells (iPS cell), neural stem cells, hematopoietic stem cells, mesenchymal stem cells, liver stem cells, pancreatic stem cells, muscle stem cells, germline stem cells, intestinal stem cells, cancer stem cells, hair follicle stem cells, and various kinds of cell lines (for example, HCT116, Huh7, HEK293 (human embryonic kidney cell), HeLa (human cervical cancer cell lines), HepG2 (human liver cancer cell lines), UT7/TPO (human leukemia cell lines), CHO (Chinese hamster ovary cell lines), MDCK, MDBK, BHK, C-33A, HT-29, AE-1, 3D9, Ns0/1, Jurkat, NIH3T3, PC12, S2, Sf9, Sf21, High Five, Vero), etc., and the coating film of the present invention has a high function of inhibiting adhesion particularly to platelets. Also, the coating film of the present invention has a high function of inhibiting adhesion particularly against a serum in which a protein or a saccharide is mixed. The coating film of the present invention has a high function of inhibiting adhesion to cells, particularly to embryonic fibroblasts. The coating film of the present invention has a high function of inhibiting adhesion to cells, particularly to mouse embryonic fibroblasts (for example, C3H10T1/2).

The terms "a function of inhibiting adhesion of a biological substance" mean, for example, when the biological substance is a platelet, it means that, in the platelet attachment test carried out by the method described in Example, a relative number of platelets attached compared to that of no coating film (%) ((a number of platelets attached (number) of Example)/(a number of platelets attached (number) of Comparative example)) is 50% or less, preferably 30% or less, and more preferably 20% or less;

when the biological substance is a protein, it means that, in the QCM-D measurement carried out by the method described in Example, a relative mass per a unit area compared to that of no coating film (%) ((a mass per a unit area (ng/cm$^2$) of Example/(a mass per a unit area (ng/cm$^2$) of Comparative example)) is 50% or less, preferably 30% or less, more preferably 20% or less; and when the biological substance is a cell, it means that, a relative absorbance compared to that of no coating film (WST O.D. 450 nm) (%) ((an absorbance (WST O.D. 450 nm) of Example)/((WST O.D. 450 nm) of Comparative example)) by a fluorescence microscope carried out by the method described in Example is 50% or less, preferably 30% or less, more preferably 20% or less.

Explanation of the Present Invention

The coating film of the present invention can be obtained by a method which comprises a process of coating a composition for forming a coating film which contains a copolymer containing a recurring unit containing an organic group of the following formula (a), a recurring unit containing an organic group of the following formula (b) and a recurring unit containing an organic group of the following formula (c):

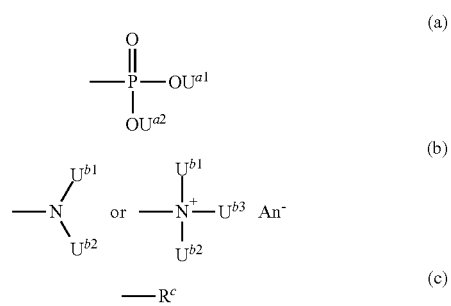

[wherein $U^{a1}$, $U^{a2}$, $U^{b1}$, $U^{b2}$ and $U^{b3}$ each independently represent a hydrogen atom or a linear or branched alkyl group having 1 to 5 carbon atoms; $R^c$ represents a linear or branched alkyl group having 4 to 18 carbon atoms, a cyclic hydrocarbon group having 3 to 10 carbon atoms, an aryl group having 6 to 10 carbon atoms, an aralkyl group having 7 to 14 carbon atoms or an aryloxyalkyl group having 7 to 14 carbon atoms (here, the above-mentioned aryl portion may be substituted by a linear or branched alkyl group having 1 to 5 carbon atoms which may be substituted by a halogen atom(s)); and $An^-$ represents an anion selected from the group consisting of a halide ion, an inorganic acid ion, a hydroxide ion and an isothiocyanate ion], and a solvent onto a substrate.

The copolymer according to the coating film of the present invention is not particularly limited as long as it is a copolymer containing the recurring unit which contains an organic group of the above-mentioned formula (a), the recurring unit which contains an organic group of the above-mentioned formula (b) and the recurring unit which contains an organic group of the above-mentioned formula (c). In the present invention, the recurring unit which contains the organic group of the above-mentioned formula (c) is different from the recurring unit which contains the organic group of the above-mentioned formula (a) and the recurring unit which contains the organic group of the above-mentioned formula (b). The polymer is desirably a material obtained by subjecting a monomer containing the organic group of the above-mentioned formula (a), a monomer containing the organic group of the above-mentioned formula (b) and a monomer containing the organic group of the above-mentioned formula (c) to radical polymerization, and a material obtained by subjecting to polycondensation or polyaddition reaction may be used. Examples of the copolymer may be mentioned a vinyl-polymerized polymer in which an olefin(s) is/are reacted, a polyamide, a polyester, a polycarbonate, a polyurethane, etc., and among these, a vinyl-polymerized polymer in which an olefin(s) is/are reacted or a (meth)acrylic polymer in which a (meth)acrylate compound(s) is/are polymerized is particularly desired.

A ratio of the recurring unit containing an organic group of the formula (a) in the copolymer according to the coating film of the present invention is 3 mol % to 80 mol %, preferably 3.5 mol % to 50 mol %, more preferably 4 mol % to 30 mol %. Incidentally, the copolymer according to the present invention may contain two or more kinds of the recurring units containing an organic group of the formula (a).

A ratio of the recurring unit containing an organic group of the formula (b) in the copolymer according to the coating film of the present invention is 3 mol % to 80 mol %, preferably 5 mol % to 70 mol %, more preferably 8 mol % to 65 mol %. Incidentally, the copolymer according to the present invention may contain two or more kinds of the recurring units containing an organic group of the formula (b).

A ratio of the recurring unit containing an organic group of the formula (c) in the copolymer according to the coating film of the present invention may be the whole remainder subtracting the ratios of the above-mentioned formulae (a) and (b) from the whole of the copolymer, or may be the remainder subtracting the total ratio of the above-mentioned formulae (a) and (b) and a fourth component mentioned below from the same, and, for example, it is 1 mol % to 90 mol %, preferably 3 mol % to 88 mol %. It is more preferably 5 mol % to 87 mol %. It is most preferably 50 mol % to 86 mol %. Incidentally, the copolymer according to the present invention may contain two or more kinds of the recurring units containing an organic group of the formula (c).

A combination of the ratios of the recurring units which contain the organic groups of the above-mentioned formula (a), the formula (b) and the formula (c) in the copolymer according to the present invention is,
preferably
3 mol % to 80 mol % of the formula (a), 3 mol % to 80 mol % of the formula (b), and 1 mol % to 90 mol % of the formula (c),
more preferably,
3.5 mol % to 50 mol % of the formula (a), 5 mol % to 70 mol % of the formula (b), and 3 mol % to 88 mol % of the formula (c),
further preferably
4 mol % to 30 mol % of the formula (a), 8 mol % to 65 mol % of the formula (b), and 5 mol % to 87 mol % of the formula (c),
and most preferably
4 mol % to 30 mol % of the formula (a), 8 mol % to 65 mol % of the formula (b), and 50 mol % to 86 mol % of the formula (c).

The solvent to be contained in the composition for forming a coating film of the present invention may be mentioned water, a phosphate buffered physiological saline (PBS) and an alcohol. The alcohol may be mentioned an alcohol having 2 to 6 carbon atoms, for example, ethanol, propanol, isopropanol, 1-butanol, 2-butanol, isobutanol, t-butanol, 1-pentanol, 2-pentanol, 3-pentanol, 1-heptanol, 2-heptanol, 2,2-dimethyl-1-propanol (=neopentyl alcohol), 2-methyl-1-propanol, 2-methyl-1-butanol, 2-methyl-2-butanol (=t-amyl alcohol), 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol and cyclohexanol, which may be used singly or a mixed solvent of these in combination, and in the viewpoint of dissolution of the copolymer, it is preferably selected from water, PBS, ethanol and propanol.

A concentration of the solid component in the composition for forming a coating film according to the present invention is desirably 0.01 to 50% by mass to form a coating film uniformly. Also, the concentration of the copolymer in the composition for forming a coating film is preferably 0.01 to 4% by mass, more preferably 0.01 to 3% by mass, particularly preferably 0.01 to 2% by mass, more preferably 0.01 to 1% by mass. If the concentration of the copolymer is 0.01% by mass or less, the concentration of the copolymer of the obtainable composition for forming a coating film is too low so that a coating film having a sufficient film thickness cannot be formed, while if it is 4% by mass or more, storage stability of the composition for forming a coating film is poor, and there is a possibility of causing deposition of the dissolved material or gelation thereof.

Further, to the composition for forming a coating film of the present invention may be added other substances within the range which does not impair the performance of the obtainable coating film depending on the necessity, in addition to the above-mentioned copolymer and the solvent. The other substances may be mentioned an antiseptic, a surfactant, a primer which heightens adhesiveness with the substrate, an antifungal agent and a saccharide, etc.

To control ion balance of the copolymer in the composition for forming a coating film according to the present invention, when the coating film of the present invention is to be obtained, a process of previously adjusting a pH of the composition for forming a coating film may be further contained. The pH adjustment may be carried out, for example, by adding a pH adjusting agent to the composition containing the above-mentioned copolymer and a solvent, to make the pH of the composition 3.0 to 13.5, preferably 3.5 to 8.5, more preferably 3.5 to 5.5, or to make the same preferably 8.5 to 13.5, more preferably 10.0 to 13.5. A kind of the pH adjusting agent which can be used and an amount thereof are optionally selected depending on the concentration of the above-mentioned copolymer, and an existing ratio of the anion and the cation, etc.

Examples of the pH adjusting agent may be mentioned an organic amine such as ammonia, diethanolamine, pyridine, N-methyl-D-glucamine, tris(hydroxymethyl)aminomethane, etc.; an alkali metal hydroxide such as potassium hydroxide, sodium hydroxide, etc.; an alkali metal halide such as potassium chloride, sodium chloride, etc.; an inorganic acid such as sulfuric acid, phosphoric acid, hydrochloric acid, carbonic acid, etc., or an alkali metal salt thereof; a quaternary ammonium cation such as choline, etc., or a mixture thereof (for example, a buffer such as a phosphate buffered physiological saline, etc.). Among these, ammonia, diethanolamine, sodium hydroxide, choline, N-methyl-D-glucamine and tris(hydroxymethyl)aminomethane are preferred, and ammonia, diethanolamine, sodium hydroxide and choline are particularly preferred.

Accordingly, the present invention relates to the composition for forming a coating film comprising (i) the copolymer containing the recurring unit which contains an organic group of the above-mentioned formula (a), the recurring unit which contains an organic group of the above-mentioned formula (b) and the recurring unit which contains an organic group of the above-mentioned formula (c), (ii) the solvent, and, if necessary, (iii) the pH adjusting agent. Specific examples of the copolymer, the solvent and the pH adjusting agent are as mentioned above.

The present invention also relates to a sol comprising the copolymer containing the recurring unit which contains an organic group of the above-mentioned formula (a), the recurring unit which contains an organic group of the above-mentioned formula (b) and the recurring unit which contains the organic group of the above-mentioned formula (c). Specific examples of the copolymer contained in the sol are as mentioned above.

The sol of the present invention preferably further contains a solvent and a pH adjusting agent. Specific examples of the solvent and the pH adjusting agent are as mentioned above. The sol of the present invention is more preferably a sol for forming a coating film, and is one embodiment of the composition for forming a coating film.

The sol of the present invention has an average particle diameter of 2 nm or more and 500 nm or less in particle diameter distribution measured by the dynamic light scattering method. More preferred average particle diameter is 2 nm or more and 400 nm or less, further preferred average particle diameter is 2 nm or more and 300 nm or less, and the most preferred average particle diameter is 2 nm or more and 200 nm or less.

The composition for forming a coating film according to the present invention is coated onto a substrate and dried to form a coating film.

The substrate for forming the coating film of the present invention may be mentioned glass, a metal containing compound or a semi-metal containing compound, activated charcoal or a resin. The metal containing compound or the semi-metal containing compound may be mentioned, for example, ceramics comprising a metal oxide as a basic component, which are a sintered body baked by a heat treatment at a high temperature, a semiconductor such as silicon, an inorganic solid material including a molded product of an inorganic compound such as a metal oxide or a semimetal oxide (silicon oxide, alumina, etc.), a metal carbide or a semi-metal carbide, a metal nitride or a semi-metal nitride (silicon nitride, etc.), a metal boride or a semi-metal boride, etc., aluminum, nickel-titanium and stainless (SUS304, SUS316, SUS316L, etc.).

The resin may be either a natural resin or a synthetic resin, and the natural resin preferably used may be mentioned cellulose, cellulose triacetate (CTA), cellulose to which dextran sulfate has been fixed, etc., while the synthetic resin preferably used may be mentioned polyacrylonitrile (PAN), polyester-based polymer alloy (PEPA), polystyrene (PS), polysulfone (PSF), polyethylene terephthalate (PET), polymethyl methacrylate (PMMA), polyvinyl alcohol (PVA), polyurethane (PU), ethylene vinyl alcohol (EVAL), polyethylene (PE), polyester (PE), polypropylene (PP), polyvinylidene fluoride (PVDF), polyether sulfone (PES), polycarbonate (PC), polyvinyl chloride (PVC), polytetrafluoroethylene (PTFE), ultrahigh molecular weight polyethylene (UHPE), poly dimethylsiloxane (PDMS), an acrylonitrile-butadiene-styrene resin (ABS), Teflon (Registered Trademark), cycloolefin polymer (COP) (for example, ZEONOR (Registered Trademark), ZEONEX (Registered Trademark) (available from ZEON CORPORATION)) or various kinds of ion exchange resins, etc., more preferably polystyrene (PS), polyether sulfone (PES), polypropylene (PP) and cycloolefin polymer (COP), and particularly preferably polystyrene (PS) and polyether sulfone (PES). The coating film of the present invention can be formed by a low temperature drying, so that it can be applied to a resin having low heat resistance, etc.

For forming the coating film of the present invention, the above-mentioned composition for forming a coating film is coated onto at least a part of the surface of the substrate. The coating method is not particularly limited, and a usual coating method such as spin coating, dip coating, a solvent casting method, etc., may be used.

The drying process of the coating film according to the present invention is carried out under the atmosphere or under vacuum, preferably at a temperature within the range of −200° C. to 200° C. According to the drying process, the solvent in the above-mentioned composition for forming a coating film is removed, and the units of the formula (a) and the formula (b) of the copolymer according to the present invention form ionic bonding to completely fix to the substrate.

The coating film may be formed by, for example, the drying at room temperature (10° C. to 35° C., for example, 25° C.), and for forming the coating film more rapidly, it may be dried at, for example, 40° C. to 50° C. In addition, a drying process at a very low temperature to low temperature (−200° C. to around −30° C.) by a freeze drying method may be used. Freeze drying is called as freeze vacuum drying, and is a method of removing a solvent under a vacuum state by sublimation by generally cooling a material to be dried with a coolant. A general coolant to be used in the freeze drying may be mentioned a mixed medium of dry ice and methanol (−78° C.), liquid nitrogen (−196° C.), etc.

If the drying temperature is −200° C. or lower, a coolant which is not in general must be used so that it lacks in versatility, and it takes a long time for drying due to sublimation of the solvent so that the efficiency is bad. If the drying temperature is 200° C. or higher, ionic bonding reaction at the surface of the coating film excessively proceeds and the surface loses a hydrophilic property, whereby a function of inhibiting adhesion of a biological substance cannot be exhibited. More preferred drying temperature is 10° C. to 180° C., and more preferred drying temperature is 25° C. to 150° C.

After the drying, to remove impurities, unreacted monomer, etc., remained on the coating film, and further to adjust ion balance of the copolymer in the film, it may be carried out a process of washing with at least one solvent selected from the group consisting of water and an aqueous solution containing an electrolyte(s). Washing is desirably washing with running water or washing with ultrasonic wave, etc. The above-mentioned water and the aqueous solution containing an electrolyte(s) may be a material heated, for example, within the range of 40° C. to 95° C. The aqueous solution containing an electrolyte(s) is preferably PBS, a physiological saline (a material containing sodium chloride alone), a Dulbecco's phosphate buffered physiological saline, a Tris buffered physiological saline, a HEPES buffered physiological saline and a Veronal buffered physiological saline, and PBS is particularly preferred. After fixation, even when the coating film is washed with water, PBS and an alcohol, etc., it does not elute and is still firmly fixed to the substrate. Even when a biological substance is attached to the formed coating film, it can be easily removed thereafter by washing with water, etc., and the surface of the substrate onto which the coating film of the present invention has been formed has a function of inhibiting adhesion of a biological substance.

Examples of the application of the coating film according to the present invention may be mentioned, for example, a coating film for a filter of an artificial dialyzer, and the coating film of the present invention has good fixing property to the synthetic resin (for example, PES, PS and PSF, etc.) used as a filter, and has good durability after fixation. A form of the substrate is not particularly limited, and may be mentioned a substrate board, fiber, particles, a gel form, a porous form, etc., and a shape of which may be a flat plate or a curved surface.

For example, when a coating film for a filter of an artificial dialyzer is to be manufactured, a liquid of the composition for forming a coating film according to the present invention is flown through the inside of the filter prepared by the above-mentioned raw material, for example, having a hollow fiber shape with a diameter of 0.1 to 500 μm, thereafter, subjecting to a drying process and a washing process (hot water (for example, 40° C. to 95° C.) washing, etc.) to manufacture the film.

If necessary, there is a case where a treatment with γ ray, ethylene oxide, an autoclave, etc., is carried out for sterilization.

A film thickness of the coating film of the present invention is preferably 10 to 1,000 Å, more preferably 10 to 500 Å, and most preferably 20 to 400 Å.

The coating film of the present invention has a function of inhibiting adhesion of a biological substance, so that it can be suitably used as a coating film for a medical substrate. It can be suitably used as, for example, a leukocyte-removing filter, a blood transfusion filter, a virus-removing filter, a micro blood clots-removing filter, a module for blood purification, an artificial heart, an artificial lung, a blood circuit, an artificial blood vessel, a blood vessel bypass tube, a medical tube, an artificial valve, a cannula, a stent, a catheter, a catheter in blood vessel, a balloon catheter, a guide wire, a suture, an indwelling needle, shunt, an artificial joint, an artificial hip joint, a blood bag, a blood reservoir, auxiliary instruments for operation, an adhesion preventing film, a wound covering material, etc. Here, the module for blood purification means a module having a function of removing wastes or a toxic substance in the blood by circulating the blood outside the body, and may be mentioned an artificial kidney, a toxin adsorption filter or column, etc.

Also, the coating film of the present invention is useful as a coating film of a cell culture vessel such as a flask, a dish, a plate, etc., or various kinds of equipment for research in which attachment of a protein is suppressed.

Further, the coating film of the present invention is also useful as a material for cosmetics, a material for a contact lens care article, a fiber finishing agent for skin care, a material for a diagnostic agent for biochemical research, a blocking agent for suppressing non-specific adsorption in an enzyme-linked immunosorbent assay (ELISA) method or a latex aggregation method which has widely been used in the clinical diagnosis, a stabilizer for stabilizing a protein such as an enzyme and an antibody, etc.

Moreover, the coating film of the present invention is also useful as a coating film for toiletry, a personally care product, a detergent, a pharmaceutical product, a quasi-drug, fiber and an antifouling material.

The copolymer contained in the composition for forming a coating film and the sol according to the present invention particularly preferably used is a copolymer containing the recurring units of the following formulae (a1), (b1) and (c1).

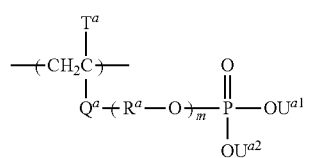
(a1)

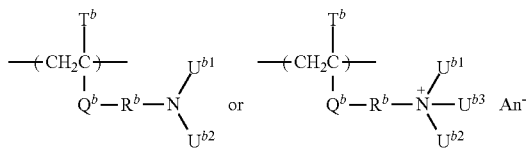
(b1)

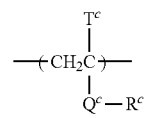
(c1)

In the formulae, $T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $Q^c$ represents a single bond, an ether bond or an ester bond, $R^a$ and $R^b$ each independently represent a linear or branched alkylene group having 1 to 10 carbon atoms which may be substituted by a halogen atom(s), $R^a$ and $R^b$ each independently represent a linear or branched alkylene group having 1 to 10 carbon atoms which may be substituted by a halogen atom(s), $R^c$ represents a linear or branched alkyl group having 4 to 18 carbon atoms, an alicyclic hydrocarbon group having 3 to 10 carbon atoms, an aryl group having 6 to 10 carbon atoms, an aralkyl group having 7 to 14 carbon atoms or an aryloxyalkyl group having 7 to 14 carbon atoms (wherein, the above-mentioned aryl portion may be substituted by a linear or branched alkyl group having 1 to 5 carbon atoms which may be substituted by a halogen atom(s)), $An^-$ represents an anion selected from the group consisting of a halide ion, an inorganic acid ion, a hydroxide ion and an isothiocyanate ion, and m represents an integer of 0 to 6.

In the formula (a1), m is an integer of 0 to 6, preferably an integer of 1 to 6, more preferably an integer of 1 to 5, and particularly preferably 1.

A ratio of the recurring unit of the formula (a1) contained in the copolymer according to the present invention is 3 mol % to 80 mol %, preferably 3.5 mol % to 50 mol %, more preferably 4 mol % to 30 mol %. Incidentally, the copolymer according to the present invention may contain two or more kinds of the recurring units of the formula (a1).

A ratio of the recurring unit of the formula (b1) contained in the copolymer according to the present invention is 3 mol % to 80 mol %, preferably 5 mol % to 70 mol %, more preferably 8 mol % to 65 mol %. Incidentally, the copolymer according to the present invention may contain two or more kinds of the recurring units of the formula (b1).

A ratio of the recurring unit of the formula (c1) contained in the copolymer according to the present invention may be the whole remainder subtracting the ratio of the above-mentioned formula (a1) and the formula (b1) from the whole of the copolymer, or may be the remainder subtracting the total ratio of the above-mentioned formula (a1) and the formula (b1) and a fourth component mentioned below from the same, and is, for example, 1 mol % to 90 mol %, preferably 3 mol % to 88 mol %, more preferably 5 mol % to 87 mol %, and most preferably 50 mol % to 86 mol %. Incidentally, the copolymer according to the present invention may contain two or more kinds of the recurring units of the formula (c1).

A combination of the ratios of the recurring units of the above-mentioned formula (a1), the formula (b1) and the formula (c1) in the copolymer according to the present invention is, preferably
3 mol % to 80 mol % of the formula (a1), 3 mol % to 80 mol % of the formula (b1), and 1 mol % to 90 mol % of the formula (c1),
more preferably,
3.5 mol % to 50 mol % of the formula (a1), 5 mol % to 70 mol % of the formula (b1), and 3 mol % to 88 mol % of the formula (c1),
further preferably
4 mol % to 30 mol % of the formula (a1), 8 mol % to 65 mol % of the formula (b1), and 5 mol % to 87 mol % of the formula (c1),
and most preferably
4 mol % to 30 mol % of the formula (a1), 8 mol % to 65 mol % of the formula (b1), and 50 mol % to 86 mol % of the formula (c1).

The present invention also relates to a copolymer obtainable by reacting (polymerizing) a monomer mixture containing compounds of the following formulae (A), (B) and (C):

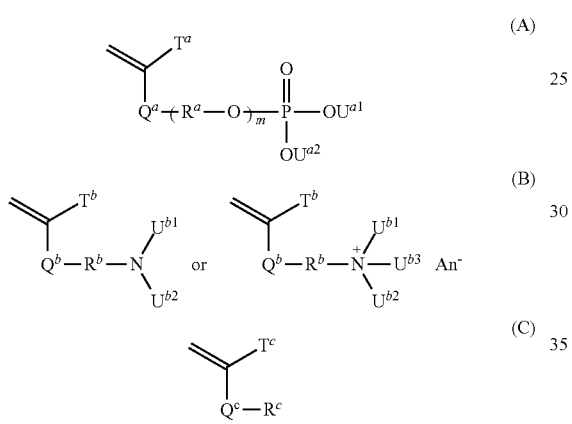

[wherein
$T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;
$Q^a$ and $Q^b$ each independently represent a single bond, an ester bond or an amide bond, $Q^c$ represents a single bond, an ether bond or an ester bond;
$R^a$ and $R^b$ each independently represent a linear or branched alkylene group having 1 to 10 carbon atoms which may be substituted by a halogen atom(s), $R^c$ represents a linear or branched alkyl group having 1 to 18 carbon atoms, a cyclic hydrocarbon group having 3 to 10 carbon atoms, an aryl group having 6 to 10 carbon atoms, an aralkyl group having 7 to 14 carbon atoms or an aryloxyalkyl group having 7 to 14 carbon atoms (here, the above-mentioned aryl portion may be substituted by a linear or branched alkyl group having 1 to 5 carbon atoms which may be substituted by a halogen atom(s));
An⁻ represents an anion selected from the group consisting of a halide ion, an inorganic acid ion, a hydroxide ion and an isothiocyanate ion; and
m represents an integer of 0 to 6]
in a solvent and a method for manufacturing the same.

$T^a$, $T^b$ and $T^c$ are each preferably a hydrogen atom, a methyl group or an ethyl group, more preferably a hydrogen atom or a methyl group. $U^{a1}$, $U^{a2}$, $U^{b1}$, $U^{b2}$ and $U^{b3}$ are each preferably a hydrogen atom, a methyl group, an ethyl group or a t-butyl group, and more preferably a hydrogen atom for $U^{a1}$ and $U^{a2}$ of the formula (a), and a hydrogen atom, a methyl group, an ethyl group or a t-butyl group for $U^{b1}$, $U^{b2}$ and $U^{b3}$ of the formula (b).

Specific examples of the above-mentioned formula (A) may be mentioned vinyl phosphonic acid, acid phosphoxy ethyl (meth)acrylate, 3-chloro-2-acid phosphoxy propyl (meth)acrylate, acid phosphoxy propyl (meth)acrylate, acid phosphoxy methyl (meth)acrylate, acid phosphoxy polyoxyethylene glycol mono(meth)acrylate and acid phosphoxy polyoxypropylene glycol mono(meth)acrylate, etc., and among these, vinyl phosphonic acid, acid phosphoxy ethyl methacrylate (=2-(methacryloyloxy)ethyl phosphate), acid phosphoxy polyoxyethylene glycol monomethacrylate and acid phosphoxy polyoxypropylene glycol monomethacrylate are preferably used.

The structural formulae of the vinyl phosphonic acid, acid phosphoxy ethyl methacrylate (=2-(methacryloyloxy)ethyl phosphate), acid phosphoxy polyoxyethylene glycol monomethacrylate and acid phosphoxy polyoxypropylene glycol monomethacrylate are shown by the following formula (A-1) to the formula (A-4), respectively.

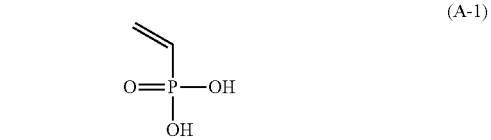

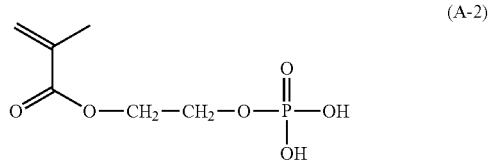

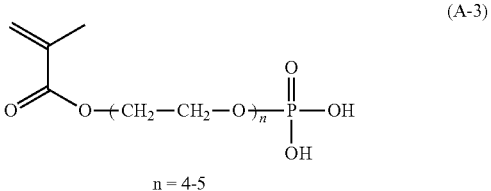

n = 4-5

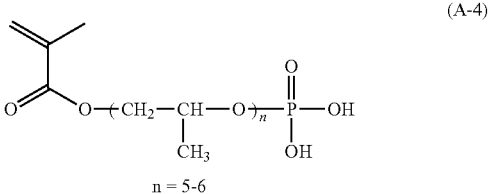

n = 5-6

Acid phosphoxy ethyl methacrylate (=2-(methacryloyloxy)ethyl phosphate) is, for example, a compound contained in product name; Phosmer M (available from Uni-Chemical Co., Ltd.) or LIGHT ESTER P-1M (available from Kyoeisha Chemical Co., Ltd.).

Acid phosphoxy polyoxyethylene glycol monomethacrylate is, for example, a compound contained in product name; Phosmer PE (available from Uni-Chemical Co., Ltd.).

Acid phosphoxy polyoxypropylene glycol monomethacrylate is, for example, a compound contained in product name; Phosmer PP (available from Uni-Chemical Co., Ltd.).

These compounds may contain a (meth)acrylate compound having two functional groups of the formula (D) or (E) mentioned later at the time of synthesis in some cases.

Specific examples of the above-mentioned formula (B) may be mentioned dimethylaminoethyl (meth)acrylate, diethylaminoethyl (meth)acrylate, dimethylaminopropyl (meth)acrylate, 2-(t-butylamino)ethyl (meth)acrylate, methacryloyl choline chloride, etc., and among these, dimethylaminoethyl (meth)acrylate, methacryloyl choline chloride or 2-(t-butylamino)ethyl (meth)acrylate is preferably used.

Structural formulae of the dimethylaminoethyl acrylate (=acrylic acid 2-(dimethylamino)ethyl), diethylaminoethyl methacrylate (=methacrylic acid 2-(diethylamino)ethyl), dimethylaminoethyl methacrylate (=methacrylic acid 2-(dimethylamino)ethyl), methacryloylcholine chloride and 2-(t-butylamino)ethyl methacrylate (=methacrylic acid 2-(t-butylamino)ethyl are shown by the following formula (B-1) to the formula (B-5), respectively.

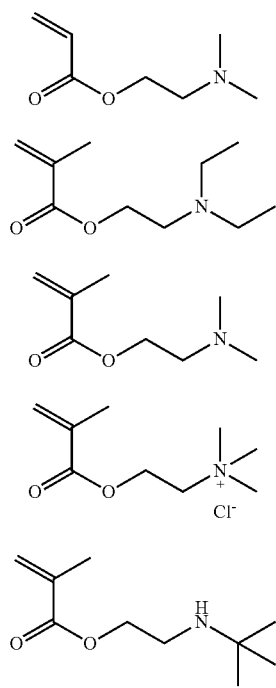

Specific examples of the above-mentioned formula (C) may be mentioned a linear or branched alkyl ester of (meth)acrylic acid such as butyl (meth)acrylate, 2-ethylhexyl (meth)acrylate, lauryl (meth)acrylate, stearyl (meth)acrylate, etc.; a cyclic alkyl ester of (meth)acrylic acid such as cyclohexyl (meth)acrylate, isobornyl (meth)acrylate, etc.; an aralkyl ester of (meth)acrylic acid such as benzyl (meth)acrylate, phenethyl (meth)acrylate, etc.; a styrene-based monomer such as styrene, methyl styrene, chloromethylstyrene, etc.; a vinyl ether-based monomer such as methyl vinyl ether, butyl vinyl ether, etc.; a vinyl ester-based monomer such as vinyl acetate, vinyl propionate, etc. Among these, butyl (meth)acrylate or cyclohexyl (meth)acrylate is preferably used.

Structural formulae of the butyl methacrylate (=methacrylic acid butyl) and cyclohexyl methacrylate (=methacrylic acid cyclohexyl) are shown by the following formula (C-1) and the formula (C-2), respectively.

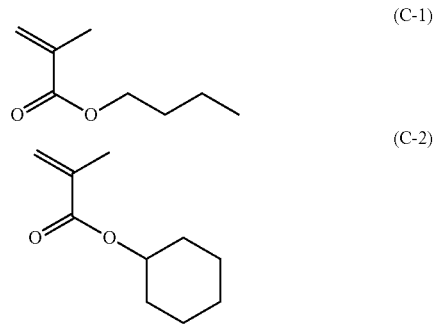

The copolymer according to the present invention may be further copolymerized with an optional fourth component. For example, as the fourth component, a (meth)acrylate compound having two or more functional groups may be copolymerized, and a part of the polymer may be partially three-dimensionally crosslinked. Such a fourth component may be mentioned, for example, a bifunctional monomer of the following formula (D) or (E):

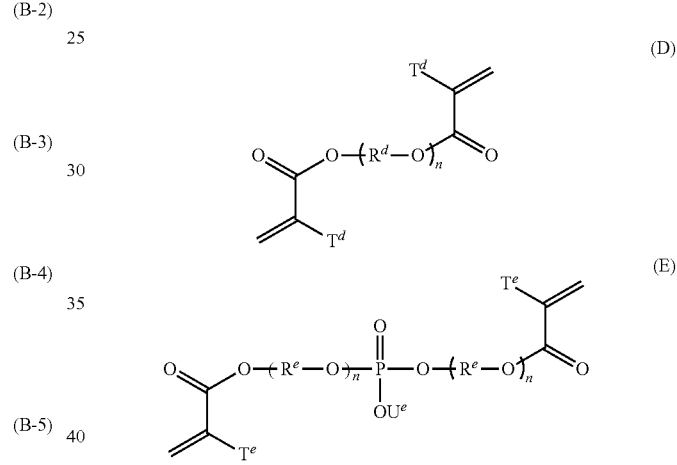

[wherein $T^d$, $T^e$ and $U^e$ each independently represent a hydrogen atom or a linear or branched alkyl group having 1 to 5 carbon atoms, $R^d$ and $R^e$ each independently represent a linear or branched alkylene group having 1 to 10 carbon atoms which may be substituted by a halogen atom(s); and n represents an integer of 1 to 6]. That is, the copolymer according to the present invention preferably contains a crosslinked structure derived from such a bifunctional monomer.

In the formula (D) and (E), $T^d$ and $T^e$ are preferably each independently a hydrogen atom, a methyl group or an ethyl group, more preferably, each independently, a hydrogen atom or a methyl group.

In the formula (E), $U^e$ is preferably a hydrogen atom, a methyl group or an ethyl group, more preferably a hydrogen atom.

In the formula (D), $R^d$ preferably represents a linear or branched alkylene group having 1 to 3 carbon atoms which may be substituted by a halogen atom(s), more preferably, each independently represents an ethylene group or a propylene group, or an ethylene group or a propylene group each substituted by one chlorine atom, and particularly preferably an ethylene group or a propylene group. Also, in the formula (D), n preferably represents an integer of 1 to 5, particularly preferably 1.

In the formula (E), $R^e$ preferably represents a linear or branched alkylene group having 1 to 3 carbon atoms which may be substituted by a halogen atom(s), more preferably, each independently represents an ethylene group or a propylene group, or an ethylene group or a propylene group each substituted by one chlorine atom, and particularly preferably an ethylene group or a propylene group. Also, in the formula (E), n preferably represents an integer of 1 to 5, particularly preferably 1.

The bifunctional monomer of the formula (D) is preferably mentioned ethylene glycol di(meth)acrylate, triethylene glycol di(meth)acrylate, propylene glycol di(meth)acrylate, or the bifunctional monomer derived from the above-mentioned formula (A-3) or (A-4), etc.

The bifunctional monomer of the formula (E) is preferably mentioned bis(methacryloyloxymethyl) phosphate, bis[(2-methacryloyloxy)ethyl] phosphate, bis[3-(methacryloyloxy)propyl] phosphate, or the bifunctional monomer derived from the above-mentioned formula (A-3) or (A-4).

In addition, as trifunctional (meth)acrylate compound, phosphynylidine tris(oxy-2,1-ethanediyl) triacrylate may be mentioned.

Among these fourth components, particularly preferred are ethylene glycol di(meth)acrylate, propylene glycol di(meth)acrylate, bis[2-(methacryloyloxy)ethyl]phosphate, bis[3-(methacryloyloxy)propyl] phosphate and among the bifunctional monomer derived from the above-mentioned formula (A-3) and (A-4), di(meth)acrylate having a recurring unit of ethylene glycol or propylene glycol and di(meth) acrylate having a recurring unit of ethylene glycol or propylene glycol via a phosphate group, and their structural formulae are shown by the following formulae (D-1) to (D-3) and the formulae (E-1) to (E-3), respectively.

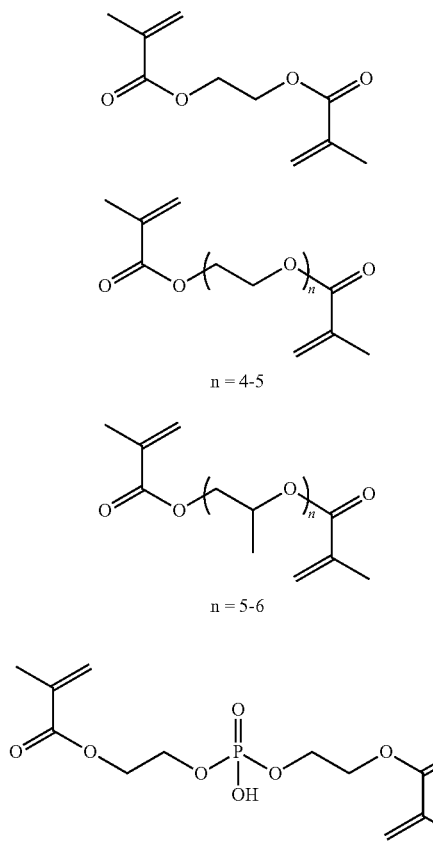

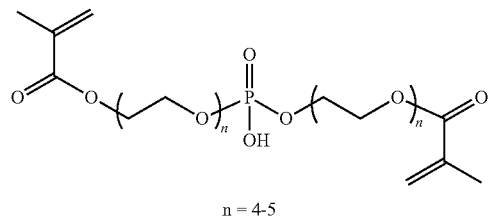

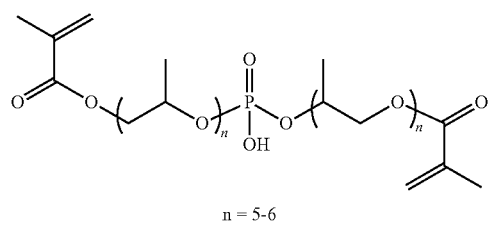

One or more kinds of these fourth components may be contained in the copolymer.

A ratio of the fourth component in the above-mentioned copolymer, for example, the cross-linked structure derived from the bifunctional monomer of the above-mentioned formula (D) or (E) is 0 mol % to 50 mol %.

A ratio of the compound of the formula (A) based on the whole monomers forming the above-mentioned copolymer is 3 mol % to 80 mol %, preferably 3.5 mol % to 50 mol %, more preferably 4 mol % to 30 mol %. In addition, the compound of the formula (A) may be two or more kinds.

A ratio of the compound of the formula (B) based on the whole monomers forming the above-mentioned copolymer is 3 mol % to 80 mol %, preferably 5 mol % to 70 mol %, more preferably 8 mol % to 65 mol %. In addition, the compound of the formula (B) may be two or more kinds.

A ratio of the compound of the formula (C) based on the whole monomers forming the above-mentioned copolymer may be the whole remainder subtracting the ratio of the above-mentioned formulae (A) and (B) from the whole monomers, or may be the remainder subtracting the total ratio of the above-mentioned formulae (A) and (B) and the above-mentioned fourth component from the same, and is, for example, 1 mol % to 90 mol %, preferably 3 mol % to 88 mol %, more preferably 5 mol % to 87 mol %, and most preferably 50 mol % to 86 mol %. In addition, the compound of the formula (C) may be two or more kinds.

The copolymer according to the present invention may be further copolymerized with an ethylenically unsaturated monomer, or a polysaccharide or a derivative thereof as an optional fifth component. Examples of the ethylenically unsaturated monomer may be mentioned one or more ethylenically unsaturated monomers selected from the group consisting of (meth)acrylic acid and an ester thereof; vinyl acetate; vinyl pyrrolidone; ethylene; vinyl alcohol; and a hydrophilic functional derivative thereof. Examples of the polysaccharide or a derivative thereof may be mentioned a cellulose-based polymer such as hydroxyalkyl cellulose (for example, hydroxyethyl cellulose or hydroxypropyl cellulose), etc., starch, dextran and curdlan.

The hydrophilic functional derivative refers to an ethylenically unsaturated monomer having a hydrophilic functional group or structure. Examples of the hydrophilic functional group or structure may be mentioned a betaine structure; an amide structure; an alkylene glycol residue; an amino group; and a sulfinyl group, etc.

The betaine structure means a monovalent or divalent group of a compound having an amphoteric center of a quaternary ammonium type cation structure and an acidic anion structure, and may be mentioned, for example, a phosphoryl choline group:

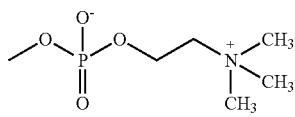

Examples of the ethylenically unsaturated monomer having such a structure may be mentioned 2-methacryloyloxyethyl phosphoryl choline (MPC), etc.

The amide structure means a group of the following formula:

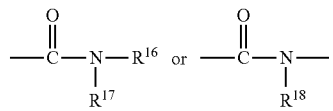

[wherein $R^{16}$, $R^{17}$ and $R^{18}$ each independently represent a hydrogen atom or an organic group (for example, a methyl group, a hydroxymethyl group or a hydroxyethyl group, etc.)]. Examples of the ethylenically unsaturated monomer having such a structure may be mentioned (meth)acrylamide, N-(hydroxymethyl) (meth)acrylamide, etc. Further, the monomer or polymer having such a structure is disclosed in, for example, JP 2010-169604A, etc.

The alkylene glycol reside means an alkyleneoxy group (-Alk-O—) which remains after the condensation reaction of the hydroxyl group(s) at the one side terminal or both terminals of the alkylene glycol (HO-Alk-OH; wherein, Alk is an alkylene group having 1 to 10 carbon atoms) with the other compound(s), and includes a poly(alkyleneoxy) group in which an alkyleneoxy unit is repeated. Examples of the ethylenically unsaturated monomer having such a structure may be mentioned 2-hydroxyethyl (meth)acrylate, methoxy polyethylene glycol (meth)acrylate, etc. Further, the monomer or polymer having such a structure is disclosed, for example, in JP 2008-533489A, etc.

The amino group means a group of the formula: —$NH_2$, —$NHR^{19}$ or —$NR^{20}R^{21}$ [wherein $R^{19}$, $R^{20}$ and $R^{21}$ each independently represent an organic group (for example, linear or branched alkyl group having 1 to 5 carbon atoms, etc.)]. The amino group in the present invention includes a quaternarized or chlorinated amino group. Examples of the ethylenically unsaturated monomer having such a structure may be mentioned dimethylaminoethyl (meth)acrylate, 2-(t-butylamino)ethyl (meth)acrylate, methacryloyl choline chloride, etc.

The sulfinyl group means a group of the following formula:

[wherein $R^{22}$ is an organic group (for example, an organic group having 1 to 10 carbon atoms, preferably an alkyl group having 1 to 10 carbon atoms which has one or more hydroxyl groups, etc.)]. The polymer having such a structure may be mentioned the copolymers disclosed in JP 2014-48278A, etc.

As the synthetic method of the copolymer according to the present invention, there may be mentioned the methods of the radical polymerization, the anion polymerization, the cation polymerization, etc., which are general synthetic methods of an acrylic polymer or a methacrylic polymer, etc., whereby a copolymer can be synthesized. As the reaction form thereof, various methods such as the solution polymerization, the suspension polymerization, the emulsion polymerization, the bulk polymerization, etc., may be employed.

The composition for forming a coating film according to the present invention may be prepared by diluting a desired copolymer with a desired solvent to a predetermined concentration.

Further, the composition for forming a coating film according to the present invention may be prepared from the varnish containing the copolymer of the present invention. As one of the embodiments, the varnish containing the copolymer of the present invention can be prepared by the manufacturing method containing a process of reacting (polymerizing) the compounds of the above-mentioned formulae (A) and (B) in a solvent with a total concentration of the both compounds of 0.01% by mass to 20% by mass.

The solvent to be used in the polymerization reaction may be water, a phosphate buffered solution or an alcohol such as ethanol, etc., or a mixed solution in which these solvents are used in combination, and desirably contains water or ethanol. Further, it is preferred to contain water or ethanol in an amount of 10% by mass or more and 100% by mass or less. Moreover, it is preferred to contain water or ethanol in an amount of 50% by mass or more and 100% by mass or less. Furthermore, it is preferred to contain water or ethanol in an amount of 80% by mass or more and 100% by mass or less. Still further, it is preferred to contain water or ethanol in an amount of 90% by mass or more and 100% by mass or less. A total amount of water and ethanol is preferably 100% by mass.

As the reaction concentration, for example, it is preferred to make the concentration of the compounds of the above-mentioned formula (A) or the formula (B) in the reaction solvent 0.01% by mass to 4% by mass. If the concentration is 4% by mass or more, for example, there is sometimes a case that the copolymer is gelled in the reaction solvent due to strong associative property possessed by the phosphate group of the formula (A). If the concentration is 0.01% by mass or less, the concentration of the obtained varnish is too low, so that it is difficult to prepare the composition for forming a coating film for obtaining a coating film having a sufficient film thickness. The concentration is more preferably 0.01% by mass to 3% by mass, for example, 3% by mass, 2% by mass or 1% by mass.

Also, in the synthesis of the copolymer according to the present invention, for example, after preparing an acidic phosphate monomer (half salt) described in the formula (1), it may be polymerized with a compound of the formula (C) to prepare the copolymer.

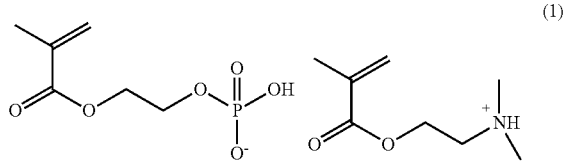

(1)

The phosphate group-containing monomer is a monomer easily associated, so that it may be added dropwise to the reaction solvent little by little so as to rapidly disperse therein when it is added dropwise to the reaction system.

Moreover, the reaction solvent may be heated (for example, 40° C. to 100° C.) to increase the solubility of the monomer and the polymer.

To proceed with the polymerization reaction efficiently, a polymerization initiator is desirably used. Examples of the polymerization initiator to be used may be mentioned 2,2'-azobis(isobutyronitrile), 2,2'-azobis(2-methylbutyronitrile), 2,2'-azobis(2,4-dimethylvaleronitrile) (product name; V-65, available from Wako Pure Chemical Industries, Ltd., 10 hour half-life temperature; 51° C.), 4,4'-azobis(4-cyanovaleric acid), 2,2'-azobis(4-methoxy-2,4-dimethylvaleronitrile), 1,1'-azobis(cyclohexane-1-carbonitrile), 1-[(1-cyano-1-methylethyl)azo]formamide, 2,2'-azobis[2-(2-imidazolin-2-yl)propane] dihydrochloride (product name; VA-044, available from Wako Pure Chemical Industries, Ltd., 10 hour half-life temperature; 44° C.), 2,2'-azobis[2-(2-imidazolin-2-yl)propane] (product name; VA-061, available from Wako Pure Chemical Industries, Ltd., 10 hour half-life temperature; 61° C.), 2,2'-azobis(2-methylpropionamidine) dihydrochloride, 2,2'-azobis(2-methyl-N-(2-hydroxyethyl)propionamide (product name; VA-086, available from Wako Pure Chemical Industries, Ltd., 10 hour half-life temperature; 86° C.), benzoyl peroxide (BPO), 2,2'-azobis(N-(2-carboxyethyl)-2-methylpropionamidine) n-hydrate (product name; VA-057, available from Wako Pure Chemical Industries, Ltd., 10 hour half-life temperature; 57° C.), 4,4'-azobis(4-cyanopentanoic acid) (product name; VA-501, available from Wako Pure Chemical Industries, Ltd.), 2,2'-azobis[2-(2-imidazolin-2-yl)propane] disulfate dihydrate (product name; VA-046B, available from Wako Pure Chemical Industries, Ltd., 10 hour half-life temperature; 46° C.), 2,2'-azobis(2-amidinopropane) dihydrochloride (product name; V-50, available from Wako Pure Chemical Industries, Ltd., 10 hour half-life temperature; 56° C.), peroxodisulfuric acid or t-butyl hydroperoxide, etc.

When solubility in water, ion balance and an interaction with the monomers are taking into consideration, it is preferred to select the material from 2,2'-azo(2-methyl-N-(2-hydroxyethyl)propionamide), 2,2'-azobis(N-(2-carboxyethyl)-2-methylpropionamidine) n-hydrate, 4,4'-azobis(4-cyanopentanoic acid), 2,2'-azobis[2-(2-imidazolin-2-yl)propane] dihydrochloride, 2,2'-azobis[2-(2-imidazolin-2-yl)propane] disulfate dihydrate, 2,2'-azobis[2-(2-imidazolin-2-yl)propane], 2,2'-azobis(2-amidinopropane) dihydrochloride and peroxodisulfuric acid.

When solubility in an organic solvent, ion balance and an interaction with the monomers are taking into consideration, it is desired to use 2,2'-azobis(2,4-dimethylvaleronitrile) or 2,2'-azobis(isobutyronitrile).

An amount of the polymerization initiator to be added is 0.05% by mass to 10% by mass based on the total weight of the monomers to be used for the polymerization.

As the reaction conditions, the polymerization reaction proceeds by heating a reaction vessel by an oil bath, etc., at 50° C. to 200° C. and stirring for 1 hour to 48 hours, more preferably at 80° C. to 150° C. for 5 hours to 30 hours to obtain the copolymer of the present invention. The reaction atmosphere is preferably a nitrogen atmosphere.

As the reaction procedure, the whole reaction substances are charged in the reaction solvent at the room temperature, and then, the polymerization may be carried out by heating to the above-mentioned temperature, or whole or a part of the mixture of the reaction substances may be added dropwise to the previously heated solvent little by little.

According to the latter reaction procedure, the varnish containing the copolymer of the present invention can be prepared by the manufacturing method comprising a process of adding dropwise a mixture containing the compounds of the above-mentioned formulae (A), (B) and (C), a solvent and a polymerization initiator to the solvent maintained at a temperature higher than the 10-hr half-life temperature of the polymerization initiator, and reacting (polymerizing) the compounds.

According to this embodiment, by employing the above-mentioned reaction procedure and the temperature conditions, a concentration of the compounds of the above-mentioned formulae (A) and (B) in the reaction solvent can be made, for example, 0.01% by mass to 10% by mass. In this embodiment, even if the concentration exceeds 4% by mass, the dropping phase and the reaction phase become transparent uniform solutions before the reaction, and gelation of the copolymer in the reaction solvent after the reaction can be suppressed. Other conditions in this embodiment are the same as mentioned above.

A weight molecular weight of the copolymer according to the present invention may be several thousand to several million or so, preferably 5,000 to 5,000,000. It is more preferably 10,000 to 2,000,000. Also, it may be either of a random copolymer, a block copolymer or a graft copolymer, there is no specific limitation in the copolymerization reaction itself for producing the copolymer, and a conventionally known method synthesized in a solution such as radical polymerization, ion polymerization, or polymerization utilizing photopolymerization, macromer or emulsion polymerization can be used. Depending on the purposes thereof to be used, any one of the copolymers of the present invention may be solely used, or a plural kinds of the copolymers may be used by mixing with optionally changing the ratios thereof.

Also, the various copolymers produced as mentioned above may be a two-dimensional polymer or a three-dimensional polymer, and is in a state of dispersing in a solution containing water. That is, in the varnish containing these polymers, it is not preferred to cause ununiform gelation or turbid precipitation, and a transparent varnish, a dispersed colloidal varnish or a sol is preferred.

The copolymer according to the present invention has both of the cation and the anion in the molecule, so that it becomes a sol by bonding the copolymers to each other due to ionic bonding in some cases. Also, as mentioned above, for example, in the case of a copolymer in which a (meth)acrylate compound(s) having two or more functional groups is/are copolymerized as a third component, a part of the copolymer is partially three-dimensionally crosslinked to form a sol in some cases.

EXAMPLES

In the following, the present invention is explained further in detail by referring to Synthetic examples and Examples, but the present invention is not limited by these.

<Measurement Method of Weight Average Molecular Weight>

A weight average molecular weight shown in the following Synthetic example is a measurement result by Gel Filtration Chromatography (hereinafter abbreviated to as GFC), or by Gel Permeation Chromatography (hereinafter abbreviated to as GPC). The measurement conditions, etc., are as follows.

(Measurement Conditions of GFC)
- Device: Prominence (manufactured by Shimadzu Corporation)
- GFC column: TSKgel GMPWXL (7.8 mm I.D.×30 cm)×2 to 3 columns
- Flow rate: 1.0 ml/min
- Eluent: Aqueous solution containing ionic substance, or a mixed solution of EtOH
- Column temperature: 40° C.
- Detector: RI
- Injection concentration: Polymer solid content 0.05 to 0.5% by mass
- Injection amount: 100 μL
- Calibration curve: Cubic approximate curve
- Standard sample: Polyethylene oxide (available from Agilent Technologies Japan, Ltd.)×10 kinds (Measurement Conditions of GPC)
- Device: HLC-8220 (manufactured by TOSOH CORPORATION)
- GPC column: Shodex [Registered Trademark] & Asahipak [Registered Trademark](manufactured by SHOWA DENKO K.K.)×3 columns
- Flow rate: 0.6 ml/min
- Eluent: N,N-dimethylformamide (DMF)
- Column temperature: 40° C.
- Detector: RI
- Injection concentration: Polymer solid content 0.05 to 0.5% by mass
- Injection amount: 100 μL
- Calibration curve: Cubic approximate curve
- Standard sample: Polystyrene (available from TOSOH CORPORATION)×10 kinds <Measurement Method of Composition of Starting Material (Phosphor-Containing Compound)>

Measurement of the concentration (% by mass) of the respective phosphor-containing compounds of the starting materials containing the phosphor-containing compound was carried out by $^{31}$P-NMR. The absolute concentration (absolute % by mass) of the respective phosphor-containing compounds contained in the starting materials was calculated by using the following mentioned standard substances.

(Measurement Conditions)
- Mode: Reverse gate decoupling mode (quantitative mode)
- Device: Varian 400 MHz
- Solvent: $CD_3OD$ (deuterated methanol) (30% by weight)
- Rotation number: 0 Hz
- Data point: 64,000
- Flip angle: 90°
- Waiting time: 70 s
- Integration times: 16 times, n=4,
- Standard substance: trimethylphosphate+$D_2O$ (75% TMP solution was prepared)

<Measurement Method of pH>
- Device: A desktop pH meter LAQUA F-72 (manufactured by HORIBA Ltd.)
- Electrode: Micro ToupH electrode 9618S
- Temperature: 25° C.±1° C.
- Conditions: Measured by directly inserting composition into electrode Synthetic Example 1

17.65 g of pure water was added to 5.00 g of acid phosphoxy ethyl methacrylate (product name; Phosmer M, available from Uni-Chemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and the mixture was sufficiently dissolved. Then, 17.65 g of ethanol, 3.82 g of 2-(dimethylamino)ethyl methacrylate (available from Tokyo Chemical Industry Co., Ltd.), 0.43 g of cyclohexyl methacrylate (available from Tokyo Chemical Industry Co., Ltd.) and 0.05 g of 2,2'-azobis(N-(2-carboxyethyl)-2-methylpropionamidine) n-hydrate (product name of Wako Pure Chemical Industries, Ltd.; VA-057, available from Wako Pure Chemical Industries, Ltd.) were successively added to the aqueous solution of Phosmer M while maintaining the temperature thereof to 20° C. or lower. The mixed solution in which the above-mentioned all materials were contained which had become uniform by sufficient stirring was introduced into a dropping funnel. On the other hand, 141.24 g of pure water was separately charged in a three-necked flask attached with a cooling tube, and nitrogen was flown therein and water was raised to reflux temperature under stirring. While maintaining this state, the dropping funnel into which the above-mentioned mixed solution had been introduced was set to the three-necked flask, the mixed solution was added dropwise into the boiled solution of pure water and ethanol over 0.5 hour. After dropwise addition, the mixture was heated under stirring with the conditions in which the above-mentioned circumstances were maintained for 24 hours to obtain 185.84 g of a varnish containing a copolymer having a solid content of about 5% by mass. The weight average molecular weight of the obtained transparent liquid by GFC was about 329, 000.

Synthetic Example 2

24.54 g of pure water was added to 5.00 g of acid phosphoxy ethyl methacrylate (product name; Phosmer M, available from Uni-Chemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and the mixture was sufficiently dissolved. Then, 10.52 g of ethanol, 3.82 g of 2-(dimethylamino)ethyl methacrylate (available from Tokyo Chemical Industry Co., Ltd.), 0.36 g of butyl methacrylate (available from Tokyo Chemical Industry Co., Ltd.) and 0.05 g of 2,2'-azobis(N-(2-carboxyethyl)-2-methylpropionamidine) n-hydrate (product name of Wako Pure Chemical Industries, Ltd.; VA-057, available from Wako Pure Chemical Industries, Ltd.) were successively added to the aqueous solution of Phosmer M while maintaining the temperature thereof to 20° C. or lower. The mixed solution in which the above-mentioned all materials were contained which had become uniform by sufficient stirring was introduced into a dropping funnel. On the other hand, 141.24 g of pure water and 7.01 g of ethanol were charged in a three-necked flask attached with a cooling tube separately from the mixed solution, and nitrogen was flown therein and water was raised to reflux temperature under stirring. While maintaining this state, the dropping funnel into which the above-mentioned mixed solution had been introduced was set to the three-necked flask, the mixed solution was added dropwise into the boiled solution of pure water and ethanol over 0.5 hour. After dropwise addition, the mixture was heated under stirring with the conditions in which the above-mentioned circumstances were maintained for 24 hours to obtain 184.51 g of a varnish containing a copolymer having a solid content of about 5% by mass. The weight average molecular weight of the obtained transparent liquid by GFC was about 245, 000.

Synthetic Example 3

To 5.00 g of acid phosphoxy ethyl methacrylate (product name; Phosmer M, available from Uni-Chemical Co., Ltd., a non-volatile component by the dryness method at 100° C. for 1 hour: 91.8%, a mixture of acid phosphoxy ethyl methacrylate (44.2% by mass), bis[2-(methacryloyloxy) ethyl] phosphate (28.6% by mass) and other substances (27.2% by mass)) were successively added 6.88 g of pure water, 61.90 g of ethanol, 8.96 g of 2-(diethylamino)ethyl methacrylate (available from Tokyo Chemical Industry Co., Ltd.), 24.06 g of butyl methacrylate (available from Tokyo Chemical Industry Co., Ltd.) and 0.19 g of 2,2'-azobis (isobutyronitrile) (available from Tokyo Chemical Industry Co., Ltd.) while maintaining the temperature thereof to 20° C. or lower. The mixed solution in which the above-mentioned all materials were contained which had become uniform by sufficient stirring was introduced into a dropping funnel. On the other hand, 27.51 g of pure water and 247.60 g of ethanol were charged in a three-necked flask attached with a cooling tube separately from the mixed solution, and nitrogen was flown therein and the mixture was raised to reflux temperature under stirring. While maintaining this state, the dropping funnel into which the above-mentioned mixed solution had been introduced was set to the three-necked flask, the mixed solution was added dropwise into the boiled solution of pure water and ethanol over 0.5 hour. After dropwise addition, the above-mentioned circumstances were maintained for 24 hours. After 24 hours, the mixture was cooled to obtain 382.10 g of a varnish containing a copolymer having a solid content of about 9.71% by mass. The weight average molecular weight at the main peak of the obtained colloidal liquid by GPC was about 30,000.

Synthetic Example 4

To 8.00 g of acid phosphoxy polyoxyethylene glycol monomethacrylate (product name; Phosmer PE, available from Uni-Chemical Co., Ltd., a non-volatile component by the dryness method at 100° C. for 1 hour: 96.4%, a mixture of acid phosphoxy polyoxyethylene glycol monomethacrylate (48.1% by mass) and other substances (51.9% by mass)) were successively added 7.11 g of pure water, 28.44 g of ethanol, 4.39 g of 2-(diethylamino)ethyl methacrylate (available from Tokyo Chemical Industry Co., Ltd.), 26.92 g of butyl methacrylate (available from Tokyo Chemical Industry Co., Ltd.) and 0.20 g of 2,2'-azobis(isobutyronitrile) (available from Tokyo Chemical Industry Co., Ltd.) while maintaining the temperature thereof to 20° C. or lower. The mixed solution in which the above-mentioned all materials were contained which had become uniform by sufficient stirring was introduced into a dropping funnel. On the other hand, 63.99 g of pure water and 255.95 g of ethanol were charged in a three-necked flask attached with a cooling tube separately from the mixed solution, nitrogen was flown therein and the mixture was raised to reflux temperature under stirring. While maintaining this state, the dropping funnel into which the above-mentioned mixed solution had been introduced was set to the three-necked flask, the mixed solution was added dropwise into the boiled solution of pure water and ethanol over 0.5 hour. After dropwise addition, the above-mentioned circumstances were maintained for 24 hours. After 24 hours, the mixture was cooled to obtain 394.99 g of a varnish containing a copolymer having a solid content of about 9.20% by mass was obtained. The weight average molecular weight at the main peak of the obtained colloidal liquid by GPC was about 36,000.

Synthetic Example 5

To 8.00 g of acid phosphoxy polyoxyethylene glycol monomethacrylate (product name; Phosmer PE, available from Uni-Chemical Co., Ltd., a non-volatile component by the dryness method at 100° C. for 1 hour: 96.4%, a mixture of acid phosphoxy polyoxyethylene glycol monomethacrylate (48.1% by mass) and other substances (51.9% by mass)) were successively added 14.59 g of pure water, 58.36 g of ethanol, 8.77 g of 2-(diethylamino)ethyl methacrylate (available from Tokyo Chemical Industry Co., Ltd.), 23.55 g of butyl methacrylate (available from Tokyo Chemical Industry Co., Ltd.) and 0.20 g of 2,2'-azobis(isobutyronitrile) (available from Tokyo Chemical Industry Co., Ltd.) while maintaining the temperature thereof to 20° C. or lower. The mixed solution in which the above-mentioned all materials were contained which had become uniform by sufficient stirring was introduced into a dropping funnel. On the other hand, 58.36 g of pure water and 233.43 g of ethanol were charged in a three-necked flask attached with a cooling tube separately from the mixed solution, nitrogen was flown therein and the mixture was raised to reflux temperature under stirring. While maintaining this state, the dropping funnel into which the above-mentioned mixed solution had been introduced was set to the three-necked flask, and the mixed solution was added dropwise into the boiled solution of pure water and ethanol over 0.5 hour. After dropwise addition, the above-mentioned circumstances were maintained for 24 hours. After 24 hours, the mixture was cooled to obtain 405.26 g of a varnish containing a copolymer having a solid content of about 9.67% by mass. The weight average molecular weight at the main peak of the obtained colloidal liquid by GPC was about 38,000.

Synthetic Example 6

To 1.00 g of acid phosphoxy ethyl methacrylate (product name; Phosmer M, available from Uni-Chemical Co., Ltd., a non-volatile component by the dryness method at 100° C. for 1 hour: 91.8%, a mixture of acid phosphoxy ethyl methacrylate (44.2% by mass), bis[2-(methacryloyloxy) ethyl] phosphate (28.6% by mass) and other substances (27.2% by mass)) were successively added 39.76 g of ethanol, 0.76 g of 2-(dimethylamino)ethyl methacrylate (available from Tokyo Chemical Industry Co., Ltd.), 3.22 g of butyl methacrylate (available from Tokyo Chemical Industry Co., Ltd.) and 0.25 g of 2,2'-azobis(2,4-dimethylvaleronitrile) (product name; V-65, available from Wako Pure Chemical Industries, Ltd.) while maintaining the temperature thereof to 20° C. or lower. The mixed solution in which the above-mentioned all materials were contained which had become uniform by sufficient stirring was introduced into a dropping funnel. On the other hand, 29.82 g of pure water and 29.82 g of ethanol were charged in a three-necked flask attached with a cooling tube separately from the mixed solution, nitrogen was flown therein and the mixture was raised to reflux temperature under stirring. While maintaining this state, the dropping funnel into which the above-mentioned mixed solution had been introduced was set to the three-necked flask, and the mixed solution was added dropwise into the boiled solution of pure water and ethanol over 0.5 hour. After dropwise addition, the above-mentioned circumstances were maintained for 24 hours. After 24 hours, the mixture was cooled to obtain 105.00 g of a varnish containing a copolymer having a solid content of about 4.50% by mass. The weight average molecular weight of the obtained transparent liquid by GPC was about 9,200.

Synthetic Example 7

While cooling 1.00 g of acid phosphoxy ethyl methacrylate (product name; Phosmer M, available from Uni-Chemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl] phosphate (28.6% by mass) and other substances (27.2% by mass)) to 20° C. or lower, 1.18 g of choline (48-50% aqueous solution: available from Tokyo Chemical Industry Co., Ltd.) and 8.49 g of pure water were added thereto and the mixture was stirred until it became uniform. To the mixed solution were successively added 1.26 g of methacryloyl choline chloride 80% aqueous solution (available from Tokyo Chemical Industry Co., Ltd.), 3.22 g of butyl methacrylate (available from Tokyo Chemical Industry Co., Ltd.), 0.03 g of 2,2'-azobis(2,4-dimethylvaleronitrile) (product name; V-65, available from Wako Pure Chemical Industries, Ltd.) and 37.33 g of ethanol while maintaining the temperature thereof to 20° C. or lower. The mixed solution in which the above-mentioned all materials were contained which had become uniform by sufficient stirring was introduced into a dropping funnel. On the other hand, 14.00 g of pure water and 55.99 g of ethanol were charged in a three-necked flask attached with a cooling tube separately from the mixed solution, nitrogen was flown therein and the mixture was raised to reflux temperature under stirring. While maintaining this state, the dropping funnel into which the above-mentioned mixed solution had been introduced was set to the three-necked flask, the mixed solution was added dropwise into the boiled solution of pure water and ethanol over 0.5 hour. After dropwise addition, the mixture was stirred under heating while maintaining the above-mentioned circumstances for 24 hours. After 24 hours, the mixture was cooled to obtain 124.00 g of a varnish containing a copolymer having a solid content of about 5.00% by mass. The weight average molecular weight of the obtained colloidal liquid by GFC was about 42,000.

Synthetic Example 8

While cooling 1.00 g of acid phosphoxy ethyl methacrylate (product name; Phosmer M, available from Uni-Chemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl] phosphate (28.6% by mass) and other substances (27.2% by mass)) to 20° C. or lower, 1.18 g of choline (48-50% aqueous solution: available from Tokyo Chemical Industry Co., Ltd.) and 15.46 g of pure water were added thereto and the mixture was stirred until it became uniform. To the mixed solution were successively added 1.26 g of methacryloyl choline chloride 80% aqueous solution (available from Tokyo Chemical Industry Co., Ltd.), 1.38 g of butyl methacrylate (available from Tokyo Chemical Industry Co., Ltd.), 0.02 g of 2,2'-azobis(2,4-dimethylvaleronitrile) (product name; V-65, available from Wako Pure Chemical Industries, Ltd.) and 16.31 g of ethanol while maintaining the mixture to 20° C. or lower. The mixed solution in which the above-mentioned all materials were contained which had become uniform by sufficient stirring was introduced into a dropping funnel. On the other hand, 24.46 g of pure water and 24.46 g of ethanol were charged in a three-necked flask attached with a cooling tube separately from the mixed solution, nitrogen was flown therein and water was raised to reflux temperature under stirring. While maintaining this state, the dropping funnel into which the above-mentioned mixed solution had been introduced was set to the three-necked flask, the mixed solution was added dropwise into the boiled solution of pure water and ethanol over 0.5 hour. After dropwise addition, the mixture was stirred under heating while maintaining the above-mentioned circumstances for 24 hours. After 24 hours, the mixture was cooled to obtain 88.00 g of a varnish containing a copolymer having a solid content of about 5.00% by mass. The weight average molecular weight of the obtained colloidal liquid by GFC was about 38,000.

Synthetic Example 9

5.69 g of choline (48-50% aqueous solution: available from Tokyo Chemical Industry Co., Ltd.) was added to 4.75 g of acid phosphoxy ethyl methacrylate (product name; Phosmer M, available from Uni-Chemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) while cooling the mixture to 35° C. or lower and the mixture was stirred until it became uniform. To the mixed solution were successively added 5.97 g of methacryloyl choline chloride 80% aqueous solution (available from Tokyo Chemical Industry Co., Ltd.), 6.54 g of butyl methacrylate (available from Tokyo Chemical Industry Co., Ltd.), 0.08 g of 2,2'-azobis(2,4-dimethylvaleronitrile) (product name; V-65, available from Wako Pure Chemical Industries, Ltd.) and 139.95 g of ethanol while maintaining the temperature thereof to 35° C. or lower. The mixed solution in which the above-mentioned all materials were contained which had become uniform by sufficient stirring was introduced into a dropping funnel. On the other hand, 103.94 g of pure water and 112.10 g of ethanol were charged in a three-necked flask attached with a cooling tube separately from the mixed solution, nitrogen was flown therein and water was raised to reflux temperature under stirring. While maintaining this state, the dropping funnel into which the above-mentioned mixed solution had been introduced was set to the three-necked flask, and the mixed solution was added dropwise into a boiled liquid of pure water and ethanol over one hour. After dropwise addition, the mixture was stirred under heating while maintaining the above-mentioned circumstances for 24 hours. After 24 hours, the mixture was cooled to obtain 379.03 g of a varnish containing a copolymer having a solid content of about 4.16% by mass. The weight average molecular weight of the obtained colloidal liquid by GFC was about 8,600.

Synthetic Example 10

While cooling 25.00 g of acid phosphoxy ethyl methacrylate (product name; Phosmer M, available from Uni-Chemical Co., Ltd., a non-volatile component by the dryness method at 100° C. for 1 hour: 91.8%, a mixture of acid phosphoxy ethyl methacrylate (44.2% by mass), bis[2-

(methacryloyloxy)ethyl] phosphate (28.6% by mass) and other substances (27.2% by mass)) to 35° C. or lower, 29.95 g of choline (48-50% aqueous solution: available from Tokyo Chemical Industry Co., Ltd.) was added thereto and the mixture was stirred until it became uniform. To the mixed solution were successively added 20.95 g of methacryloyl choline chloride 80% aqueous solution (available from Tokyo Chemical Industry Co., Ltd.), 28.67 g of butyl methacrylate (available from Tokyo Chemical Industry Co., Ltd.), 0.70 g of 2,2'-azobis(2,4-dimethylvaleronitrile) (product name; V-65, available from Wako Pure Chemical Industries, Ltd.) and 110.84 g of ethanol while maintaining the temperature thereof to 35° C. or lower. Further, an aqueous solution in which 0.70 g of 2,2'-azobis(N-(2-carboxyethyl)-2-methylpropionamidine) n-hydrate (product name of Wako Pure Chemical Industries, Ltd.; VA-057, available from Wako Pure Chemical Industries, Ltd.) had been dissolved in 27.71 g of pure water was added to the above-mentioned solution while maintaining the temperature thereof to 35° C. or lower, the mixed solution in which the above-mentioned all materials were contained which had become uniform by sufficient stirring was introduced into a dropping funnel. On the other hand, 56.81 g of pure water and 131.62 g of ethanol were charged in a three-necked flask attached with a cooling tube separately from the mixed solution, nitrogen was flown therein and water was raised to reflux temperature under stirring. While maintaining this state, the dropping funnel into which the above-mentioned mixed solution had been introduced was set to the three-necked flask, and the mixed solution was added dropwise into a boiled liquid of pure water and ethanol over one hour. After dropwise addition, the mixture was stirred under heating while maintaining the above-mentioned circumstances for 24 hours. After 24 hours, the mixture was cooled to obtain 432.97 g of a varnish containing a copolymer having a solid content of about 19.86% by mass. The weight average molecular weight of the obtained colloidal liquid by GFC was about 8,500.

Synthetic Example 11

To 1.00 g of acid phosphoxy ethyl methacrylate (product name; Phosmer M, available from Uni-Chemical Co., Ltd., a non-volatile component by the dryness method at 100° C. for 1 hour: 91.8%, a mixture of acid phosphoxy ethyl methacrylate (44.2% by mass), bis[2-(methacryloyloxy) ethyl] phosphate (28.6% by mass) and other substances (27.2% by mass)) were successively added 30.59 g of ethanol, 0.76 g of 2-(dimethylamino)ethyl methacrylate (available from Tokyo Chemical Industry Co., Ltd.), 2.07 g of butyl methacrylate (available from Tokyo Chemical Industry Co., Ltd.) and 0.19 g of 2,2'-azobis(2,4-dimethylvaleronitrile) (product name; V-65, available from Wako Pure Chemical Industries, Ltd.) while maintaining the temperature thereof to 20° C. or lower. The mixed solution in which the above-mentioned all materials were contained which had become uniform by sufficient stirring was introduced into a dropping funnel. On the other hand, 22.94 g of pure water and 22.94 g of ethanol were charged in a three-necked flask attached with a cooling tube separately from the mixed solution, nitrogen was flown therein and the mixture was raised to reflux temperature under stirring. While maintaining this state, the dropping funnel into which the above-mentioned mixed solution had been introduced was set to the three-necked flask, and the mixed solution was added dropwise into the boiled solution of pure water and ethanol over 0.5 hour. After dropwise addition, the above-mentioned circumstances were maintained for 24 hours. After 24 hours, the mixture was cooled to obtain 80.49 g of a turbid copolymer varnish having a solid content of about 4.9% by mass. The weight average molecular weight at the main peak of the obtained varnish by GPC was about 10,000.

Comparative Synthetic Example 1

68.88 g of pure water was added to 10.00 g of acid phosphoxy ethyl methacrylate (product name; Phosmer M, available from Uni-Chemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and the mixture was sufficiently dissolved. Then, 29.52 g of ethanol, 7.63 g of 2-(dimethylamino)ethyl methacrylate (available from Tokyo Chemical Industry Co., Ltd.) and 0.09 g of 2,2'-azobis(N-(2-carboxyethyl)-2-methylpropionamidine) n-hydrate (product name of Wako Pure Chemical Industries, Ltd.; VA-057, available from Wako Pure Chemical Industries, Ltd.) were successively added to the aqueous solution of Phosmer M while maintaining the temperature thereof to 20° C. or lower. The mixed solution in which the above-mentioned all materials were contained which had become uniform by sufficient stirring was introduced into a dropping funnel. On the other hand, 373.89 g of pure water and 29.52 g of ethanol were charged in a three-necked flask attached with a cooling tube separately from the mixed solution, and nitrogen was flown therein and the mixture was raised to reflux temperature under stirring. While maintaining this state, the dropping funnel into which the above-mentioned mixed solution had been introduced was set to the three-necked flask, the mixed solution was added dropwise into the boiled solution of pure water and ethanol over 0.5 hour. After dropwise addition, the mixture was heated under stirring with the conditions in which the above-mentioned circumstances were maintained for 24 hours to obtain 509.60 g of a varnish containing a copolymer having a solid content of about 3.5% by mass. The weight average molecular weight of the obtained transparent liquid by GFC was about 280, 000.

(Preparation of Silicon Wafer)

A commercially available silicon wafer for evaluating a semiconductor was used as such.

(PES Film)

A film (about 0.1 mm) of a commercially available polyether sulfone (PES), prepared by the bar coating method, which had been cut to about 1 cm square was made a PES film.

(Manufacture of QCM Sensor (PES))

An Au-deposited quartz crystal resonator (Q-Sense, QSX304) was washed for 10 minutes by using a UV/ozone washing device (UV253E, manufactured by Filgen, Inc.), and immediately thereafter, it was dipped in a solution in which 0.1012 g of 1-decanethiol (available from Tokyo Chemical Industry Co., Ltd.) had been dissolved in 100 ml of ethanol for 24 hours. After the surface of the sensor was washed with ethanol, it was naturally dried, and a varnish in which 1.00 g of poly(oxy-1,4-phenylenesulfonyl-1,4-phenylene) (available from Aldrich Corporation) had been dissolved in 99.00 g of 1,1,2,2-tetrachloroethane was spin coated by a spin coater at the film sensor side with 3,500 rpm for 30 sec, and dried at 205° C. for 1 min to manufacture a QCM sensor (PES).

(Manufacture of QCM Sensor (PS))

An Au-deposited quartz crystal resonator (Q-Sense, QSX304) was washed for 10 minutes by using a UV/ozone washing device (UV253E, manufactured by Filgen, Inc.), and immediately thereafter, it was dipped in a solution in which 0.0772 g of 2-aminoethanethiol (available from Tokyo Chemical Industry Co., Ltd.) had been dissolved in 1,000 ml of ethanol for 24 hours. After the surface of the sensor was washed with ethanol, it was naturally dried, and a varnish in which 1.00 g of polystyrene (available from Aldrich Corporation) had been dissolved in 99.00 g of toluene was spin coated by a spin coater at the film sensor side with 3,500 rpm for 30 sec, and dried at 120° C. for 1 min to manufacture a QCM sensor (PS).

Example 1

To 1.00 g of the varnish containing the copolymer obtained in the above-mentioned Synthetic example 1 were added 10.78 g of pure water and 4.89 g of ethanol, and the mixture was thoroughly stirred to prepare a composition for forming a coating film. A pH thereof was 5.2. The above-mentioned silicon wafer or PES film was dipped in the obtained composition for forming a coating film, and dried in an oven at 45° C. for 12 hours. Thereafter, the uncured composition for forming a film attached onto the coating film was sufficiently washed with PBS and pure water to obtain a silicon wafer or a PES film onto which the coating film has been formed. By using the above-mentioned silicon wafer, when a film thickness of the coating film was confirmed by an optical interference film thickness meter, then, it was 30 Å.

In addition, the above-mentioned composition for forming a coating film was spin coated onto a QCM sensor (PES) with 3,500 rpm/30 sec, and as a drying process, it was baked in an oven at 45° C. for 12 hours. Thereafter, as a washing process, excessively attached uncured composition for forming a coating film was washed with PBS and ultrapure water each twice, to obtain a surface-treated QCM sensor (PES).

Example 2

To 1.00 g of the varnish containing the copolymer obtained in the above-mentioned Synthetic example 2 were added 10.78 g of pure water and 4.89 g of ethanol, and the mixture was thoroughly stirred to prepare a composition for forming a coating film. A pH thereof was 5.3. In the same manner as in Example 1, a silicon wafer, a PES film or a surface-treated QCM sensor (PES) onto which a coating film has been formed was obtained. By using the above-mentioned silicon wafer, when a film thickness of the coating film was confirmed by an optical interference film thickness meter, then, it was 81 Å.

Example 3

To 6.50 g of the varnish containing the copolymer obtained in the above-mentioned Synthetic example 3 were added 203.88 g of ethanol and 0.17 g of aqueous ammonia (28% aqueous solution, available from KANTO CHEMICAL CO., INC.), and the mixture was thoroughly stirred to prepare a composition for forming a coating film. A pH thereof was 10.3. In the same manner as in Example 1, a silicon wafer, a PES film or a surface-treated QCM sensor (PES) onto which a coating film has been formed was obtained. By using the above-mentioned silicon wafer, when a film thickness of the coating film was confirmed by an optical interference film thickness meter, then, it was 120 Å.

Example 4

To 6.50 g of the varnish containing the copolymer obtained in the above-mentioned Synthetic example 4 were added 192.83 g of ethanol and 0.22 g of aqueous ammonia (28% aqueous solution, available from KANTO CHEMICAL CO., INC.), and the mixture was thoroughly stirred to prepare a composition for forming a coating film. A pH thereof was 11.2 In the same manner as in Example 1, a silicon wafer, a PES film or a surface-treated QCM sensor (PES) onto which a coating film has been formed was obtained. By using the above-mentioned silicon wafer, when a film thickness of the coating film was confirmed by an optical interference film thickness meter, then, it was 82 Å.

Example 5

To 6.50 g of the varnish containing the copolymer obtained in the above-mentioned Synthetic example 5 were added 203.02 g of ethanol and 0.27 g of aqueous ammonia (28% aqueous solution, available from KANTO CHEMICAL CO., INC.), and the mixture was thoroughly stirred to prepare a composition for forming a coating film. A pH thereof was 11.2. In the same manner as in Example 1, a silicon wafer, a PES film or a surface-treated QCM sensor (PES) onto which a coating film has been formed was obtained. By using the above-mentioned silicon wafer, when a film thickness of the coating film was confirmed by an optical interference film thickness meter, then, it was 119 Å.

Example 6

To 9.00 g of the varnish containing the copolymer obtained in the above-mentioned Synthetic example 6 were added 0.10 g of choline (48-50% aqueous solution: available from Tokyo Chemical Industry Co., Ltd.) and 141.00 g of ethanol, and the mixture was thoroughly stirred to prepare a composition for forming a coating film. A pH thereof was 12.8. In the same manner as in Example 1, a silicon wafer or a surface-treated QCM sensor (PES, PS) onto which a coating film has been formed was obtained. By using the above-mentioned silicon wafer, when a film thickness of the coating film was confirmed by an optical interference film thickness meter, then, it was 109 Å.

Example 7

To 9.00 g of the varnish containing the copolymer obtained in the above-mentioned Synthetic example 7 were added 0.13 g of choline (48-50% aqueous solution: available from Tokyo Chemical Industry Co., Ltd.) and 141.00 g of ethanol, and the mixture was thoroughly stirred to prepare a composition for forming a coating film. A pH thereof was 13.2. In the same manner as in Example 1, a silicon wafer or a surface-treated QCM sensor (PES, PS) onto which a coating film has been formed was obtained. By using the above-mentioned silicon wafer, when a film thickness of the coating film was confirmed by an optical interference film thickness meter, then, it was 57 Å.

Example 8

To 9.00 g of the varnish containing the copolymer obtained in the above-mentioned Synthetic example 8 were added 0.18 g of choline (48-50% aqueous solution: available from Tokyo Chemical Industry Co., Ltd.) and 141.00 g of ethanol, and the mixture was thoroughly stirred to prepare a composition for forming a coating film. A pH thereof was 12.6. In the same manner as in Example 1, a silicon wafer or a surface-treated QCM sensor (PES, PS) onto which a coating film has been formed was obtained. By using the above-mentioned silicon wafer, when a film thickness of the coating film was confirmed by an optical interference film thickness meter, then, it was 44 Å.

Example 9

To 18.00 g of the varnish containing the copolymer obtained in the above-mentioned Synthetic example 9 were added 0.57 g of 1 mol/L hydrochloric acid (1N) (available from KANTO CHEMICAL CO., INC.), 17.06 g of pure water and 39.82 g of ethanol, and the mixture was thoroughly stirred to prepare a composition for forming a coating film. A pH thereof was 3.6. In the same manner as in Example 1, a silicon wafer or a surface-treated QCM sensor (PS) onto which a coating film has been formed was obtained. By using the above-mentioned silicon wafer, when a film thickness of the coating film was confirmed by an optical interference film thickness meter, then, it was 51 Å.

Example 10

To 8.00 g of the varnish containing the copolymer obtained in the above-mentioned Synthetic example 10 were added 1.03 g of 1 mol/L hydrochloric acid (1N) (available from KANTO CHEMICAL CO., INC.), 45.26 g of pure water and 105.62 g of ethanol, and the mixture was thoroughly stirred to prepare a composition for forming a coating film. A pH thereof was 3.5. In the same manner as in Example 1, a silicon wafer or a surface-treated QCM sensor (PS) onto which a coating film has been formed was obtained. By using the above-mentioned silicon wafer, when a film thickness of the coating film was confirmed by an optical interference film thickness meter, then, it was 54 Å.

Example 11

To 10.00 g of the varnish containing the copolymer obtained in the above-mentioned Synthetic example 10 were added 1.19 g of 1 mol/L hydrochloric acid (1N) (available from KANTO CHEMICAL CO., INC.), 26.78 g of pure water and 62.54 g of ethanol, and the mixture was thoroughly stirred to prepare a composition for forming a coating film. A pH thereof was 3.6. In the same manner as in Example 1, a silicon wafer or a surface-treated QCM sensor (PS) onto which a coating film has been formed was obtained. By using the above-mentioned silicon wafer, when a film thickness of the coating film was confirmed by an optical interference film thickness meter, then, it was 112 Å.

Example 12

To 50.00 g of the varnish containing the copolymer obtained in the above-mentioned Synthetic example 10 were added 1.74 g of 1 mol/L hydrochloric acid (1N) (available from KANTO CHEMICAL CO., INC.), 45.00 g of pure water and 105.00 g of ethanol, and the mixture was thoroughly stirred to prepare a composition for forming a coating film. A pH thereof was 3.7. In the same manner as in Example 1, a silicon wafer or a surface-treated QCM sensor (PS) onto which a coating film has been formed was obtained. By using the above-mentioned silicon wafer, when a film thickness of the coating film was confirmed by an optical interference film thickness meter, then, it was 165 Å.

Example 13

To 5.00 g of the varnish containing the copolymer obtained in the above-mentioned Synthetic example 10 were added 1.29 g of citric acid (available from KANTO CHEMICAL CO., INC.), 28.53 g of pure water and 66.55 g of ethanol, and the mixture was thoroughly stirred to prepare a composition for forming a coating film. A pH thereof was 3.5. In the same manner as in Example 1, a silicon wafer or a surface-treated QCM sensor (PS) onto which a coating film has been formed was obtained. By using the above-mentioned silicon wafer, when a film thickness of the coating film was confirmed by an optical interference film thickness meter, then, it was 359 Å.

Example 14

To 5.00 g of the varnish containing the copolymer obtained in the above-mentioned Synthetic example 10 were added 1.85 g of acetic acid (available from KANTO CHEMICAL CO., INC.), 28.53 g of pure water and 66.55 g of ethanol, and the mixture was thoroughly stirred to prepare a composition for forming a coating film. A pH thereof was 3.5. In the same manner as in Example 1, a silicon wafer or a surface-treated QCM sensor (PS) onto which a coating film has been formed was obtained. By using the above-mentioned silicon wafer, when a film thickness of the coating film was confirmed by an optical interference film thickness meter, then, it was 291 Å.

Example 15

To 5.00 g of the varnish containing the copolymer obtained in the above-mentioned Synthetic example 10 were added 1.55 g of malic acid (available from KANTO CHEMICAL CO., INC.), 28.53 g of pure water and 66.55 g of ethanol, and the mixture was thoroughly stirred to prepare a composition for forming a coating film. A pH thereof was 3.5. In the same manner as in Example 1, a silicon wafer or a surface-treated QCM sensor (PS) onto which a coating film has been formed was obtained. By using the above-mentioned silicon wafer, when a film thickness of the coating film was confirmed by an optical interference film thickness meter, then, it was 342 Å.

Example 16

To 4.00 g of the varnish containing the copolymer obtained in the above-mentioned Synthetic example 10 were added 0.57 g of 1 mol/L hydrochloric acid (1N) (available from KANTO CHEMICAL CO., INC.), 0.40 g of citric acid (available from KANTO CHEMICAL CO., INC.), 22.47 g of pure water and 53.74 g of ethanol, and the mixture was thoroughly stirred to prepare a composition for forming a coating film. A pH thereof was 3.5. In the same manner as in Example 1, a silicon wafer or a surface-treated QCM sensor (PS) onto which a coating film has been formed was obtained. By using the above-mentioned silicon wafer, when a film thickness of the coating film was confirmed by an optical interference film thickness meter, then, it was 300 Å.

Comparative Example 1

The above-mentioned PES film was used as such.

Comparative Example 2

The above-mentioned QCM sensor (PES) was used as such.

Comparative Example 3

To 1.00 g of the varnish containing the copolymer obtained in the above-mentioned Comparative synthetic example 1 were added 7.27 g of pure water and 3.39 g of ethanol, and the mixture was thoroughly stirred to prepare a composition for forming a coating film. In the same manner as in Example 1, a silicon wafer, a PES film or a surface-treated QCM sensor (PES, PS) onto which a coating film has been formed was obtained. By using the above-mentioned silicon wafer, when a film thickness of the coating film was confirmed by an optical interference film thickness meter, then, it was 44 Å.

Comparative Example 4

The above-mentioned QCM sensor (PS) was used as such.

[Platelet Attachment Test]
(Preparation of Platelet Solution)

With 0.5 mL of a 3.8% by mass sodium citrate solution was mixed 4.5 mL of blood collected from a healthy volunteer, and platelet-rich plasma (PRP) at an upper layer was recovered by centrifugal separation [Refrigerated Centrifuge 5900 (manufactured by Kubota Corporation), at 1,000 rpm for 10 min and room temperature]. Subsequently, centrifugal separation (the above-mentioned Centrifuge, 3500 rpm/10 min, room temperature) of a lower layer was performed to recover platelet-poor plasma (PPP) at an upper layer. A number of the platelets of the PRP was counted by a multi-item automatic Hematology Analyzer (XT-2000i, manufactured by Sysmex Corporation), and a platelet concentration of the PRP was adjusted to be $30 \times 10^4$ cells/μL by using the PPP.

(Platelet Attachment Test)

PES films of the respective Examples and Comparative examples were provided to 24-well flat bottom microplate (manufactured by Corning Inc.). Into the well of the plate to which these substrates were provided was added 300 μL of the PRP solution which has been adjusted to the above-mentioned platelet concentration. At the state of maintaining the carbon dioxide concentration to 5%, these were allowed to stand in a $CO_2$ incubator at 37° C. for 24 hours. After lapsing a predetermined allowing time, the PRP in the plate was removed, and the plate was washed five times with each 3 mL of PBS. Thereafter, 2 mL of a PBS solution containing 2.5% by volume of glutaraldehyde was added thereto, allowed to stand at 4° C. over day and night, then, the PBS solution of glutaraldehyde was removed, and the plate was washed five times with each 3 mL of ultrapure water (Milli-Q water). Further, the plate was washed three times with each 1 mL of 70% ethanol-water (v/v), and air-dried.

[Measurement of Number of Attached Platelets]

To the PES films of the respective Examples and Comparative example which had been subjected to the above-mentioned platelet attachment test were deposited Pt—Pd for 1 minute by using ion sputter (E-1030, manufactured by Hitachi High Technologies Corporation). Thereafter, attachment of the platelets was observed by an electron microscope (S-4800, manufactured by Hitachi High Technologies Corporation) with 1,000-fold. Number of the attached platelets at the five portions (area per one portion: length 95 μm×breadth 126.5 μm=11,385 [μm$^2$]) from the center portion of the PES film within a radius of 2 mm was counted by the electron microscope. By averaging the counted values of the respective portions, it was made a number of attached platelets. The results are shown in the following Table 1.

TABLE 1

|  | Number of platelets attached (number) |
| --- | --- |
| Example 1 | 3 |
| Example 2 | 1 |
| Example 3 | 30 |
| Example 4 | 14 |
| Example 5 | 22 |
| Comparative example 1 | 159 |

[Protein Attachment Test; QCM-D Measurement]

The surface-treated QCM sensors (PES, PS) obtained in the respective Examples and Comparative examples were attached to a dissipation type quartz resonator microbalance QCM-D (E4, manufactured by Q-Sense Co.), and PBS was flown until a stable base line has been established in which change in the frequency became 1 Hz or less in one hour. Next, the frequency of the stabilized base line was made 0 Hz and PBS was flown for about 10 minutes. Subsequently, a solution in which fibrinogen had been diluted to 100 μg/ml with PBS, or a solution in which 15 wt % of fetal bovine serum (FBS), L-Glutamine, penicillin and streptomycin as antibiotics had been added to 41010-Basal Medium Eagle (BME), no Glutamine (available from Thermo Fisher Scientific Inc.) was flown for about 30 minutes, thereafter, PBS was again flown for about 20 minutes, and then, a shift (Δf) of an adsorption induced frequency at the eleventh overtone was read. By using Q-Tools (manufactured by Q-Sense Co.) for analysis, a shift (Δf) of the adsorption induced frequency is converted into a mass (ng/cm$^2$) per a unit surface area of a shift (Δf) of the adsorption induced frequency explained by the Sauerbrey's formula and shown as an attached amount of the biological substance in Table 2. As compared to Comparative examples, Examples showed low adsorption amounts of various kinds of proteins with one or two digits. Incidentally, fibrinogen was made a PES sensor as a substance to be adsorbed, and the biological substance derived from FBS was made a PS sensor, respectively

TABLE 2

| | Mass (ng/cm$^2$) per unit surface area | |
| --- | --- | --- |
| | Fibrinogen PES sensor | Biological substance derived from FBS PS sensor |
| Example 1 | 2 | — |
| Example 2 | 10 | — |
| Example 3 | 24 | — |
| Example 4 | 11 | — |
| Example 5 | 8 | — |
| Example 6 | 59 | 73 |
| Example 7 | 78 | 74 |
| Example 8 | 41 | 41 |
| Example 9 | — | 57 |
| Example 10 | — | 5 |
| Example 11 | — | 5 |
| Example 12 | — | 4 |

TABLE 2-continued

| | Mass (ng/cm²) per unit surface area | |
|---|---|---|
| | Fibrinogen PES sensor | Biological substance derived from FBS PS sensor |
| Example 13 | — | 9 |
| Example 14 | — | 8 |
| Example 15 | — | 40 |
| Example 16 | — | 21 |
| Comparative example 2 | 1641 | — |
| Comparative example 3 | 304 | 170 |
| Comparative example 4 | — | 622 |

(Preparation of Cell Culture Coating Plate)

By using the compositions for forming a coating film prepared in Examples or Comparative examples, a coating film was formed to a well of 96-well flat bottom cell culture plate (manufactured by BD Biosciences, #351172) by the coating method mentioned below.

The coating method is that 200 μL of the above-mentioned composition for forming a coating film was added to each well, and after allowing to stand for 60 minutes, excess liquid was removed and the remaining liquid was dried at 50° C. overnight. Thereafter, 200 μL of sterilized water per one well was added and then removed to carry out washing. Washing was further carried out twice in the same manner.

As a positive control sample, a commercially available cell low adhesion plate (available from Corning Inc., #3474) was used.

(Preparation of Cells)

The cells used were mouse embryonic fibroblasts C3H10T1/2 (available from DS Pharma Biomedical Co., Ltd.). The medium to be used for culture the cells was a BME medium (available from Thermo Fisher Scientific Inc.) containing 10% FBS (available from HyClone Laboratories, Inc.) and an L-glutamine-penicillin-streptomycin stabilized solution (available from SIGMA-ALDRICH Co. LLC.). The cells were stationarily cultured in a $CO_2$ incubator at 37° C. in the state of maintaining a 5% carbon dioxide concentration, by using a petri dish (10 mL of culture medium) having a diameter of 10 cm for 2 days or longer. Subsequently, the cells were washed with 5 ml of PBS, then, 1 mL of a trypsin-EDTA solution (available from Invitrogen Co.) was added thereto to peel the cells, and the cells were suspended in 10 mL of the above-mentioned medium, respectively. This suspension was centrifuged (manufactured by TOMY SEIKO CO., LTD., Type No. LC-200, 1,000 rpm/3 min, room temperature), then, the supernatant was removed, and the above-mentioned medium was added to prepare a cell suspension.

(Cell Attachment Experiment)

To the plate prepared as mentioned above were added each 100 μL of the respective cell suspension so that it became 2×10⁴ cells/well. Thereafter, in the state of maintaining the 5% carbon dioxide concentration, it was allowed to stand in a $CO_2$ incubator at 37° C. for 4 days.

(Observation of Cell Attachment)

After 4 days from the culture, attachment of the cells to the coated 96-well flat bottom cell culture plate was compared based on the observation by an inverted microscope (CKX31 manufactured by Olympus Corporation). In addition, 10 μL of Cell Counting Kit-8 solution (available from Dojindo Laboratories) was added per each well, and it was allowed to stand in a $CO_2$ incubator at 37° C. for 2 hours. Thereafter, an absorbance at 450 nm was measured by an absorbance meter (SpectraMax, manufactured by Molecular Devices, LLC.). The results are shown in the following Table 3.

TABLE 3

| Absorbance by fluorescent microscope (WST O.D.450 nm) | |
|---|---|
| | Attached amount of mouse embryonic fibroblasts |
| No coating film | 1.037 |
| #3474 (Positive control) | 0.015 |
| Example 1 | 0.218 |
| Example 2 | 0.066 |
| Example 3 | 0.020 |

As shown in Table 3, it could be shown that no cell was attached to the plate to which the coating film had been attached of the present application.

[Measurement of Particle Diameter by Dynamic Light Scattering Method]

Measurements of a sol particle diameter in each of the respective compositions for forming a coating film of the respective Examples were carried out by using a dynamic light scattering photometer (DLS, manufactured by Otsuka Electronics Co., Ltd., product name: DLS-8000DLTKY). The results are shown in Table 4.

TABLE 4

| | Average particle diameter (nm) |
|---|---|
| Example 4 | 15 |
| Example 5 | 19 |
| Example 8 | 54 |

The invention claimed is:

1. A composition for forming a coating film, wherein the film has a function of inhibiting adhesion of a biological substance, which comprises (i) a copolymer which contains a recurring unit containing an organic group of the following formula (a), a recurring unit containing an organic group of the following formula (b) and a recurring unit containing an organic group of the following formula (c):

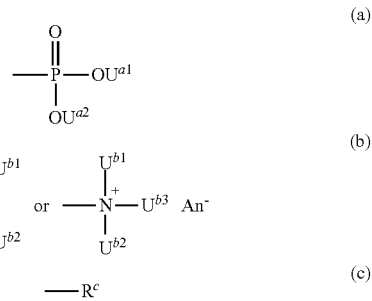

wherein
$U^{a1}$, $U^{a2}$, $U^{b1}$, $U^{b2}$ and $U^{b3}$ each independently represent a hydrogen atom or a linear or branched alkyl group having 1 to 5 carbon atoms;
$R^c$ represents a linear or branched alkyl group having 4 to 18 carbon atoms, a cyclic hydrocarbon group having 3 to 10 carbon atoms, an aralkyl group having 7 to 14 carbon atoms or an aryloxyalkyl group having 7 to 14 carbon atoms, where the above-mentioned aryl portion may be substituted by a linear or branched alkyl group having 1 to 5 carbon atoms which may be substituted by a halogen atom(s); and An⁻ represents an anion selected from the group consisting of a halide ion, an inorganic acid ion, a hydroxide ion and an isothiocyanate ion, and (ii) a solvent, wherein the copolymer is present in the composition at a concentration of 0.01% to 4% by mass.

2. The composition according to claim 1, wherein the copolymer contains recurring units of the following formulae (a1), (b1) and (c1):

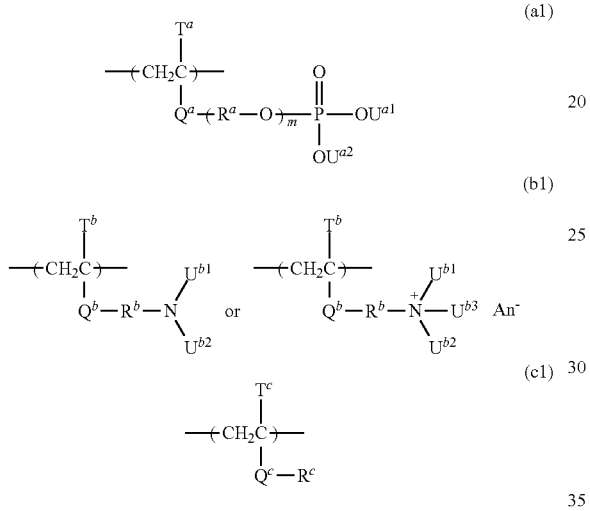

wherein $T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;

$Q^a$ and $Q^b$ each independently represent a single bond, an ester bond or an amide bond, $Q^c$ represents a single bond, an ether bond or an ester bond;

$R^a$ and $R^b$ each independently represent a linear or branched alkylene group having 1 to 10 carbon atoms which may be substituted by a halogen atom(s), $R^c$ represents a linear or branched alkyl group having 4 to 18 carbon atoms, an alicyclic hydrocarbon group having 3 to 10 carbon atoms, an aralkyl group having 7 to 14 carbon atoms or an aryloxyalkyl group having 7 to 14 carbon atoms, where the above-mentioned aryl portion may be substituted by a linear or branched alkyl group having 1 to 5 carbon atoms which may be substituted by a halogen atom(s);

An⁻ represents an anion selected from the group consisting of a halide ion, an inorganic acid ion, a hydroxide ion and an isothiocyanate ion; and m represents an integer of 0 to 6.

3. A coating film, wherein the film has a function of inhibiting adhesion of a biological substance, obtained by a method which comprises a process of coating a composition for forming a coating film onto a surface, wherein the composition comprises (1) a copolymer containing a recurring unit containing an organic group of the following formula (a), a recurring unit containing an organic group of the following formula (b) and a recurring unit containing an organic group of the following formula (c):

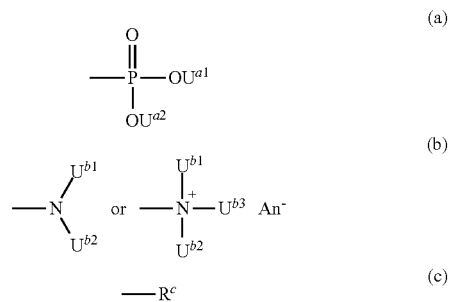

wherein $U^{a1}$, $U^{a2}$, $U^{b1}$, $U^{b2}$ and $U^{b3}$ each independently represent a hydrogen atom or a linear or branched alkyl group having 1 to 5 carbon atoms;

$R^c$ represents a linear or branched alkyl group having 4 to 18 carbon atoms, an alicyclic hydrocarbon group having 3 to 10 carbon atoms, an aralkyl group having 7 to 14 carbon atoms or an aryloxyalkyl group having 7 to 14 carbon atoms, where the above-mentioned aryl portion may be substituted by a linear or branched alkyl group having 1 to 5 carbon atoms which may be substituted by a halogen atom(s); and An⁻ represents an anion selected from the group consisting of a halide ion, an inorganic acid ion, a hydroxide ion and an isothiocyanate ion, and (2) a solvent, wherein the composition is adjusted to have a pH of from 8.5 to 13.5.

4. The coating film according to claim 3, wherein the copolymer contains recurring units of the following formulae (a1), (b1) and (c1):

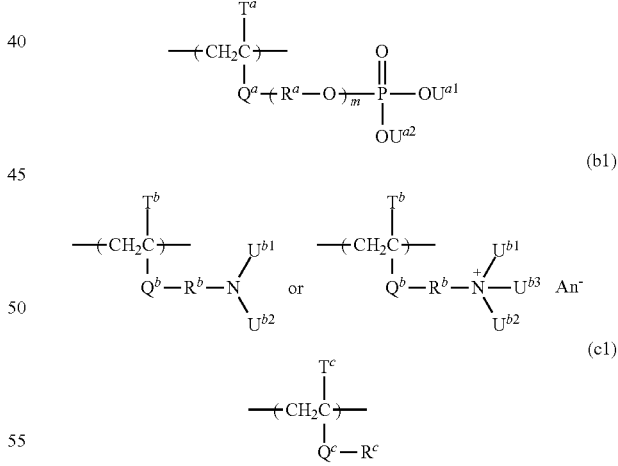

wherein $T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;

$Q^a$ and $Q^b$ each independently represent a single bond, an ester bond or an amide bond, $Q^c$ represents a single bond, an ether bond or an ester bond;

$R^a$ and $R^b$ each independently represent a linear or branched alkylene group having 1 to 10 carbon atoms which may be substituted by a halogen atom(s), $R^c$ represents a linear or branched alkyl group having 4 to 18 carbon atoms, an alicyclic hydrocarbon group having 3 to 10 carbon atoms, an aralkyl group having 7 to 14 carbon atoms or an aryloxyalkyl group having 7 to 14 carbon atoms, where the above-mentioned aryl portion may be substituted by a linear or branched alkyl group having 1 to 5 carbon atoms which may be substituted by a halogen atom(s);

An⁻ represents an anion selected from the group consisting of a halide ion, an inorganic acid ion, a hydroxide ion and an isothiocyanate ion; and m represents an integer of 0 to 6.

5. The coating film according to claim 3, wherein the method further comprises a process of washing the film obtained after a drying process by at least one kind of a solvent selected from the group consisting of water and an aqueous solution containing an electrolyte(s).

6. A sol which comprises (1) a copolymer containing a recurring unit containing an organic group of the following formula (a), a recurring unit containing an organic group of the following formula (b) and a recurring unit containing an organic group of the following formula (c):

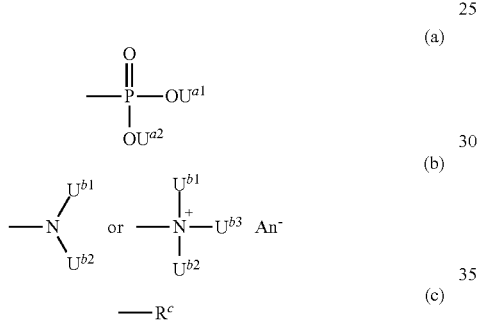

wherein $U^{a1}$, $U^{a2}$, $U^{b1}$, $U^{b2}$ and $U^{b3}$ each independently represent a hydrogen atom or a linear or branched alkyl group having 1 to 5 carbon atoms;

$R^c$ represents a linear or branched alkyl group having 4 to 18 carbon atoms, an alicyclic hydrocarbon group having 3 to 10 carbon atoms, an aralkyl group having 7 to 14 carbon atoms or an aryloxyalkyl group having 7 to 14 carbon atoms, where the above-mentioned aryl portion may be substituted by a linear or branched alkyl group having 1 to 5 carbon atoms which may be substituted by a halogen atom(s); and An⁻ represents an anion selected from the group consisting of a halide ion, an inorganic acid ion, a hydroxide ion and an isothiocyanate ion, and (2) a solvent, wherein the sol has a pH of from 8.5 to 13.5.

7. The sol according to claim 6, wherein an average particle diameter in particle diameter distribution measured by a dynamic light scattering method is 2 nm or more and 500 nm or less.

8. A method for manufacturing a coating film, wherein the film has a function of inhibiting adhesion of a biological substance, comprising a process of coating a composition for forming a coating film onto a surface, wherein the composition comprises (1) a copolymer containing a recurring unit containing an organic group of the following formula (a), a recurring unit containing an organic group of the following formula (b) and a recurring unit containing an organic group of the following formula (c):

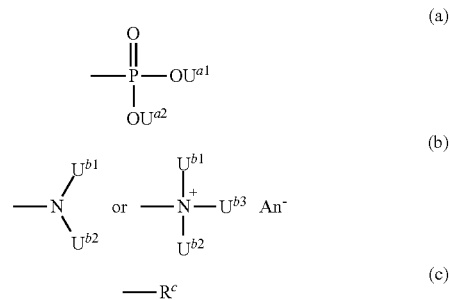

wherein $U^{a1}$, $U^{a2}$, $U^{b1}$, $U^{b2}$ and $U^{b3}$ each independently represent a hydrogen atom or a linear or branched alkyl group having 1 to 5 carbon atoms;

$R^c$ represents a linear or branched alkyl group having 4 to 18 carbon atoms, a cycloalkyl group having 3 to 8 carbon atoms, an aralkyl group having 7 to 14 carbon atoms or an aryloxyalkyl group having 7 to 14 carbon atoms, where, the above-mentioned aryl portion may be substituted by a linear or branched alkyl group having 1 to 5 carbon atoms which may be substituted by a halogen atom(s); and An⁻ represents an anion selected from the group consisting of a halide ion, an inorganic acid ion, a hydroxide ion and an isothiocyanate ion, and (2) a solvent, wherein the composition is adjusted to have a pH of from 8.5 to 13.5.

9. A method for producing a varnish containing a copolymer which comprises a process of adding dropwise a mixture containing compounds of the following formulae (A), (B) and (C):

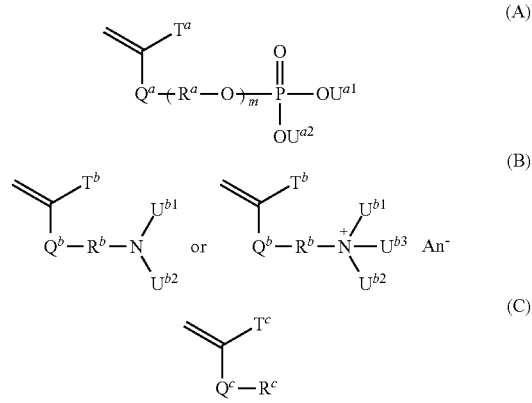

wherein $T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;

$Q^a$ and $Q^b$ each independently represent a single bond, an ester bond or an amide bond, $Q^c$ represents a single bond, an ether bond or an ester bond;

$R^a$ and $R^b$ each independently represent a linear or branched alkylene group having 1 to 10 carbon atoms which may be substituted by a halogen atom(s), $R^c$ represents a linear or branched alkyl group having 4 to 18 carbon atoms, an alicyclic hydrocarbon group having 3 to 10 carbon atoms, an aralkyl group having 7 to 14 carbon atoms or an aryloxyalkyl group having 7 to 14 carbon atoms, where, the above-mentioned aryl portion may be substituted by a linear or branched alkyl group having 1 to 5 carbon atoms which may be substituted by a halogen atom(s);

$An^-$ represents an anion selected from the group consisting of a halide ion, an inorganic acid ion, a hydroxide ion and an isothiocyanate ion; and m represents an integer of 0 to 6, a solvent and a polymerization initiator to a solvent which has been maintained at a temperature higher than a 10 hour half-life temperature of the polymerization initiator, and polymerizing the mixture of compounds to form a varnish comprising the copolymer and a solvent, and adjusting the varnish to have a pH of from 8.5 to 13.5.

10. A method for producing a composition comprising a copolymer which comprises a process of polymerizing a monomer mixture containing a solvent and at least compounds of the following formulae (A), (B) and (C):

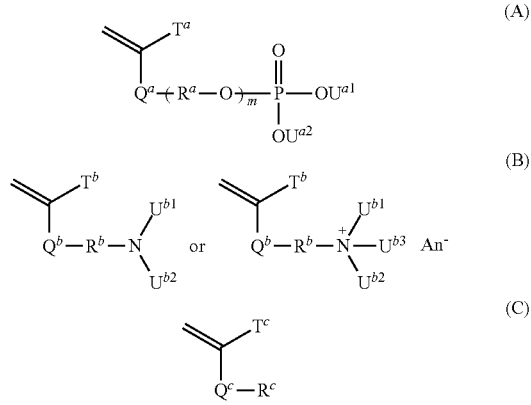

wherein $T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;

$Q^a$ and $Q^b$ each independently represent a single bond, an ester bond or an amide bond, $Q^c$ represents a single bond, an ether bond or an ester bond;

$R^a$ and $R^b$ each independently represent a linear or branched alkylene group having 1 to 10 carbon atoms which may be substituted by a halogen atom(s), $R^c$ represents a linear or branched alkyl group having 1 to 18 carbon atoms, a cyclic hydrocarbon group having 3 to 10 carbon atoms, an aralkyl group having 7 to 14 carbon atoms or an aryloxyalkyl group having 7 to 14 carbon atoms, where the above-mentioned aryl portion may be substituted by a linear or branched alkyl group having 1 to 5 carbon atoms which may be substituted by a halogen atom(s);

$An^-$ represents an anion selected from the group consisting of a halide ion, an inorganic acid ion, a hydroxide ion and an isothiocyanate ion; and m represents an integer of 0 to 6, to form a composition comprising the copolymer and the solvent, and adjusting the composition to have a pH of from 8.5 to 13.5.

11. The producing method according to claim 10, wherein the copolymer is obtained by polymerizing a monomer mixture which further contains a compound of the following formula (D) or (E):

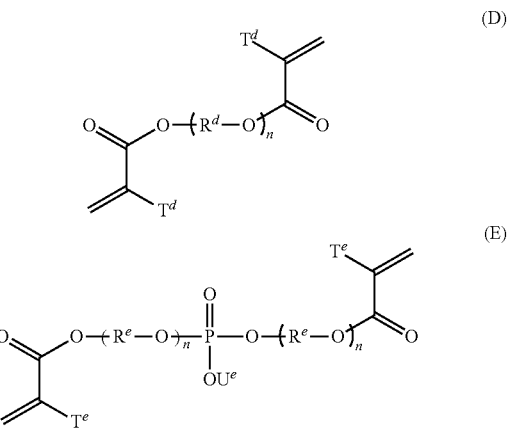

wherein $T^d$, $T^e$ and $U^e$ each independently represent a hydrogen atom or a linear or branched alkyl group having 1 to 5 carbon atoms;

$R^d$ and $R^e$ each independently represent a linear or branched alkylene group having 1 to 10 carbon atoms which may be substituted by a halogen atom(s); and n represents an integer of 1 to 6.

12. A method for producing a sol which comprises a process of polymerizing a monomer mixture containing a solvent and at least compounds of the following formulae (A), (B) and (C):

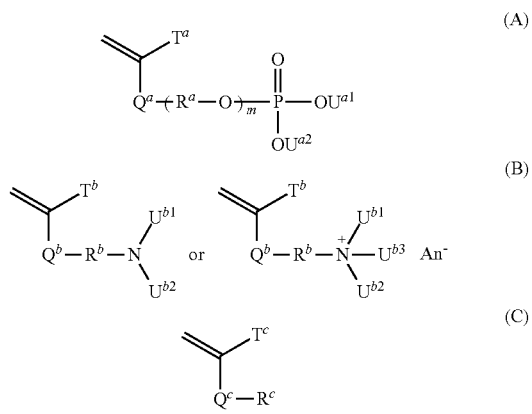

wherein $T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;

$Q^a$ and $Q^b$ each independently represent a single bond, an ester bond or an amide bond, $Q^c$ represents a single bond, an ether bond or an ester bond;

$R^a$ and $R^b$ each independently represent a linear or branched alkylene group having 1 to 10 carbon atoms which may be substituted by a halogen atom(s), $R^c$ represents a linear or branched alkyl group having 1 to 18 carbon atoms, a cyclic hydrocarbon group having 3 to 10 carbon atoms, atoms, where the above-mentioned aryl portion may be substituted by a linear or branched alkyl group having 1 to 5 carbon atoms which may be substituted by a halogen atom(s);

An⁻ represents an anion selected from the group consisting of a halide ion, an inorganic acid ion, a hydroxide ion and an isothiocyanate ion; and m represents an integer of 0 to 6, to form a sol comprising a copolymer and a solvent, and adjusting the sol to have a pH of from 8.5 to 13.5.

13. The coating film according to claim 4, wherein the method further comprises a process of washing the film obtained after a drying process by at least one kind of a solvent selected from the group consisting of water and an aqueous solution containing an electrolyte(s).

14. The method for manufacturing a coating film according to claim 8, wherein the method further comprises a process of washing the film obtained after a drying process by at least one kind of a solvent selected from the group consisting of water and an aqueous solution containing an electrolyte(s).

15. The method for manufacturing a coating film according to claim 8, wherein the copolymer contains recurring units of the following formulae (a1), (b1) and (c1):

(a1)

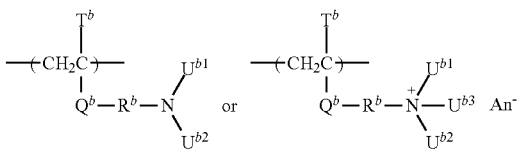

(b1)

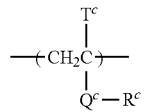

(c1)

wherein $T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;

$Q^a$ and $Q^b$ each independently represent a single bond, an ester bond or an amide bond, $Q^c$ represents a single bond, an ether bond or an ester bond;

$R^a$ and $R^b$ each independently represent a linear or branched alkylene group having 1 to 10 carbon atoms which may be substituted by a halogen atom(s), $R^c$ represents a linear or branched alkyl group having 4 to 18 carbon atoms, an alicyclic hydrocarbon group having 3 to 10 carbon atoms, an aralkyl group having 7 to 14 carbon atoms or an aryloxyalkyl group having 7 to 14 carbon atoms, where the above-mentioned aryl portion may be substituted by a linear or branched alkyl group having 1 to 5 carbon atoms which may be substituted by a halogen atom(s);

An⁻ represents an anion selected from the group consisting of a halide ion, an inorganic acid ion, a hydroxide ion and an isothiocyanate ion; and m represents an integer of 0 to 6.

16. The method for manufacturing a coating film according to claim 15, wherein the method further comprises a process of washing the film obtained after a drying process by at least one kind of a solvent selected from the group consisting of water and an aqueous solution containing an electrolyte(s).

17. The method according to claim 12, wherein an average particle diameter in particle diameter distribution measured by a dynamic light scattering method is 2 nm or more and 500 nm or less.

* * * * *